(12) United States Patent
Hallberg

(10) Patent No.: US 10,375,660 B2
(45) Date of Patent: Aug. 6, 2019

(54) SYSTEM AND METHOD FOR SYNCHRONIZED DISTRIBUTED DATA COLLECTION

(71) Applicant: Sharp Laboratories of America (SLA), Inc., Camas, WA (US)

(72) Inventor: Bryan Hallberg, Vancouver, WA (US)

(73) Assignee: Sharp Laboratories of America, Inc., Vancouver, WA (US)

( * ) Notice: Subject to any disclaimer, the term of this patent is extended or adjusted under 35 U.S.C. 154(b) by 428 days.

(21) Appl. No.: 15/355,152

(22) Filed: Nov. 18, 2016

(65) Prior Publication Data

US 2017/0078988 A1 Mar. 16, 2017

Related U.S. Application Data

(63) Continuation-in-part of application No. 15/155,943, filed on May 16, 2016, which is a continuation-in-part (Continued)

(51) Int. Cl.
*H04W 48/20* (2009.01)
*H04W 56/00* (2009.01)
(Continued)

(52) U.S. Cl.
CPC ......... *H04W 56/001* (2013.01); *A61B 5/1121* (2013.01); *A61B 5/4528* (2013.01);
(Continued)

(58) Field of Classification Search
CPC ....... H04B 7/204; H04B 7/212; H04W 48/00; H04W 48/16; H04W 48/18; H04W 48/20; H04W 56/00; H04W 72/00; H04W 72/02; H04W 72/044; H04W 72/0473; H04W 72/12

See application file for complete search history.

(56) References Cited

U.S. PATENT DOCUMENTS 8,270,414 B2 9/2012 Oi et al.
9,137,849 B1 9/2015 Wright
(Continued)

FOREIGN PATENT DOCUMENTS

WO WO2012/038234 3/2012

*Primary Examiner* — Blane J Jackson
(74) *Attorney, Agent, or Firm* — ScienBiziP, P.C.

(57) ABSTRACT

A system and method are provided for distributed data collection synchronization. Provided are communicating data generation units (DGUs) capable of data storage, having consumable power resources. In response to the DGUs comparing their availability and power resources, a master and slave DGUs are selected, and the slave DGUs synchronize their data collection to a common timing reference supplied by their master DGU. One example of consumable power is battery power. A first DGU may select itself as a master DGU in response to either waiting a first predetermined duration of time after reset, or receiving no link status message from a master DGU for a second predetermined duration of time. Alternatively, a slave first DGU may compare its own available power resources to the available power resources of its master second DGU and select itself as the master DGU when the available power resources of the first DGU are greater.

30 Claims, 15 Drawing Sheets

Related U.S. Application Data of application No. 15/091,869, filed on Apr. 6, 2016, now abandoned, which is a continuation-in-part of application No. 14/873,946, filed on Oct. 2, 2015, now Pat. No. 9,846,040, which is a continuation-in-part of application No. 14/742,852, filed on Jun. 18, 2015.

(51) Int. Cl.
| | | |
|---|---|---|
| *H04W 72/02* | (2009.01) | |
| *H04W 72/12* | (2009.01) | |
| *A61B 5/00* | (2006.01) | |
| *A61B 5/11* | (2006.01) | |
| *H04W 84/20* | (2009.01) | |

(52) U.S. Cl.
CPC ............ *A61B 5/742* (2013.01); *A61B 5/0024* (2013.01); *A61B 5/1114* (2013.01); *A61B 5/7475* (2013.01); *A61B 2562/0219* (2013.01); *H04W 84/20* (2013.01)

(56) References Cited

U.S. PATENT DOCUMENTS

| | | | |
|---|---|---|---|
| 9,143,309 B2* | 9/2015 | Fraser | H04M 1/00 |
| 2014/0341073 A1* | 11/2014 | Abraham | H04W 48/18 |
| | | | 370/254 |
| 2017/0142741 A1* | 5/2017 | Kaur | H04W 56/002 |

* cited by examiner

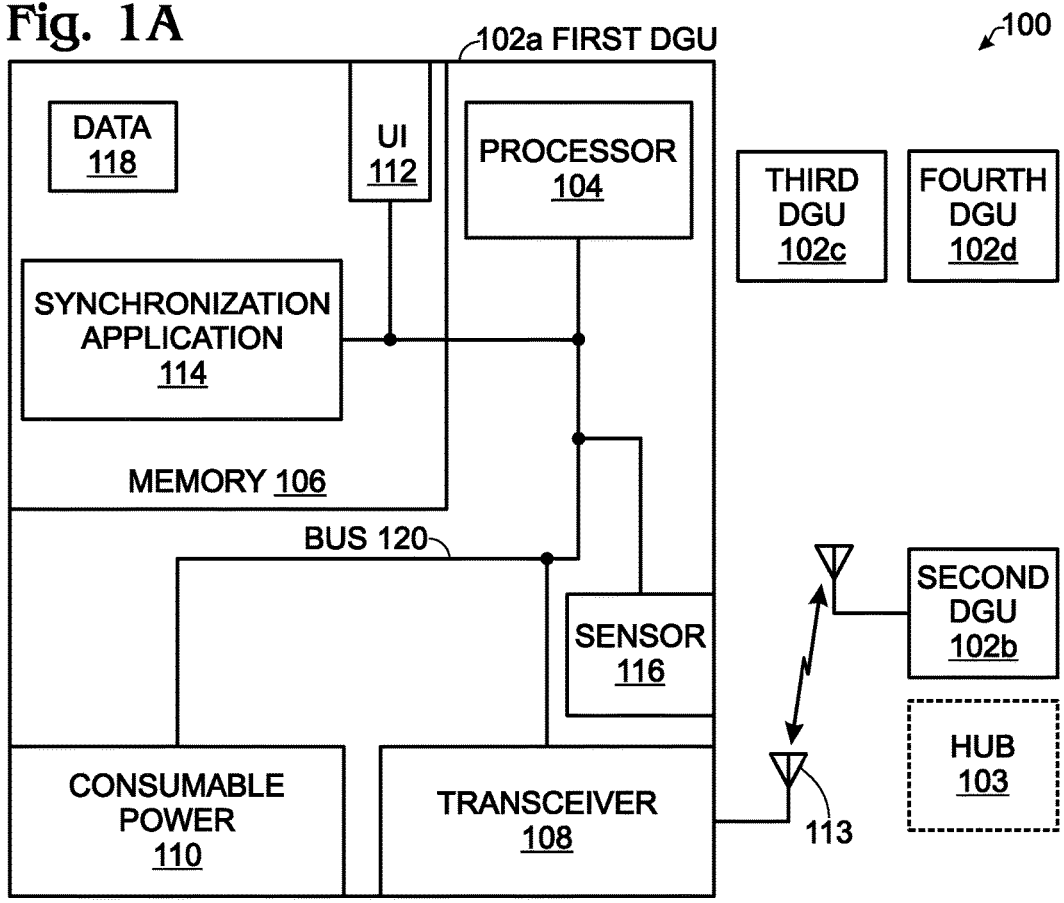
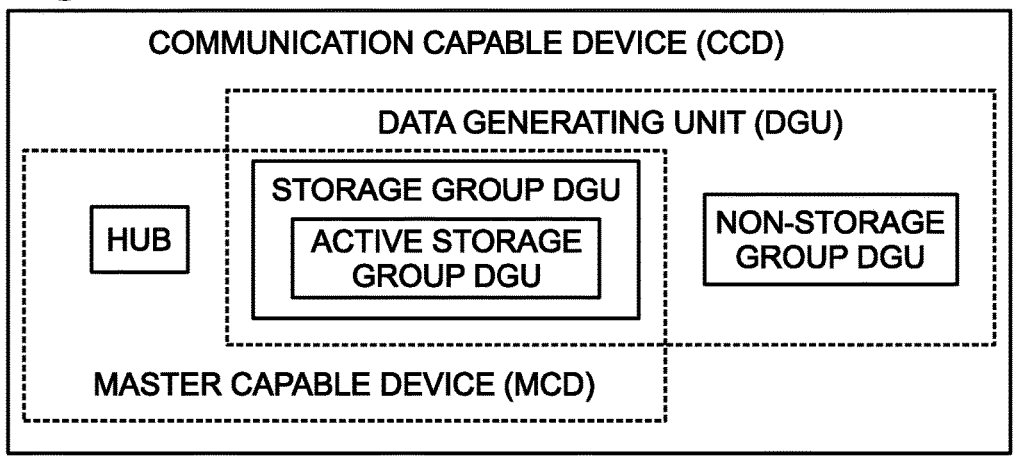

EXAMPLE 1

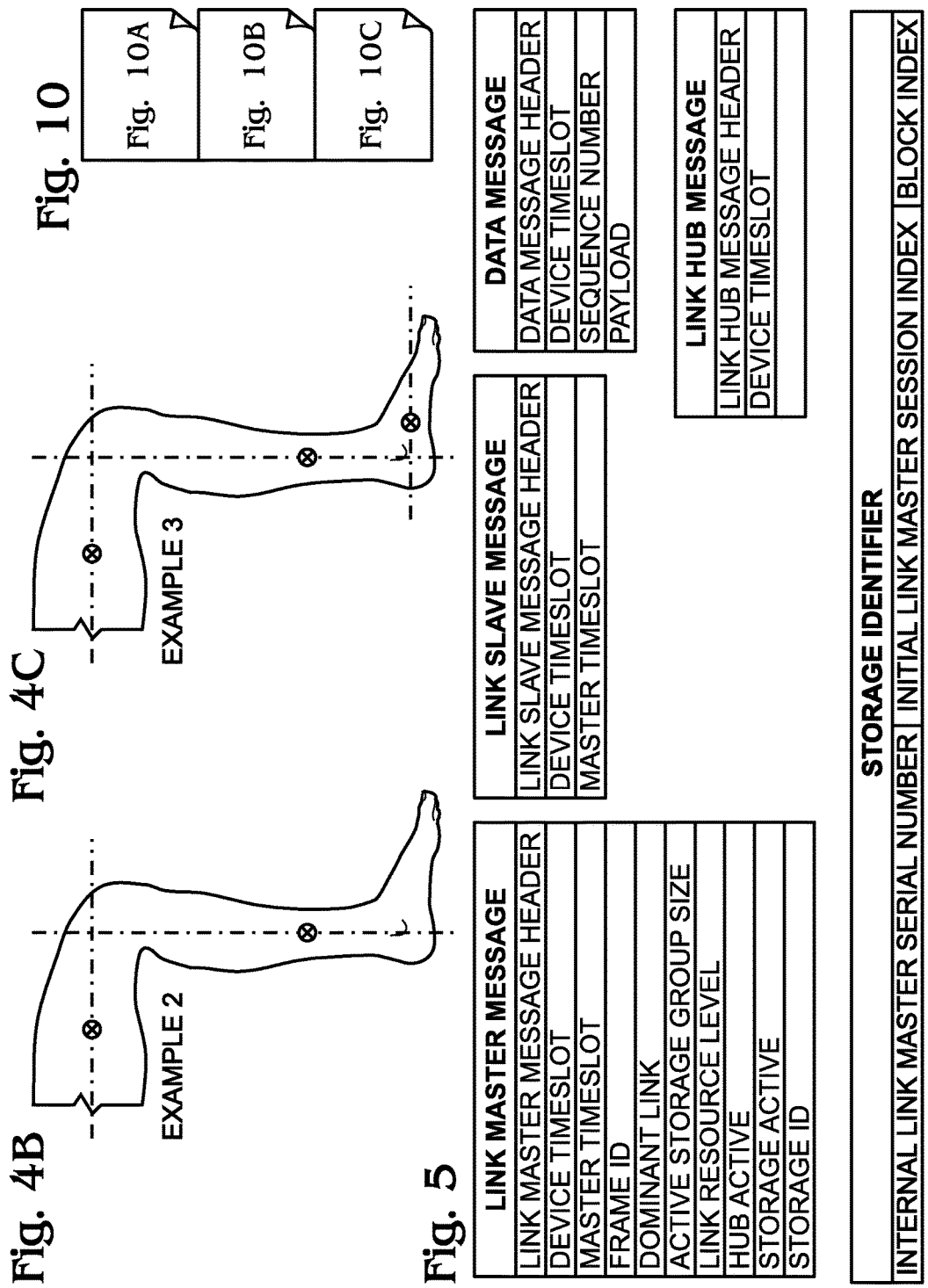

Fig. 10A

| RULE # | FROM STATE | TO STATE | RULE DESCRIPTION |
|---|---|---|---|
| 1 | DEVICE RESET | LINK STANDBY | DEVICE HAS UNASSIGNED TIMESLOT OR DEVICE IS NOT IN STORAGE GROUP |
| 2 | DEVICE RESET | LINK UNGROUPED | DEVICE HAS ASSIGNED TIMESLOT AND DEVICE IN STORAGE GROUP AND RECORD ENABLED |
| 3 | ANY | LINK STANDBY | HUB COMMUNICATION TIMED OUT AND (DEVICE HAS UNASSIGNED TIMESLOT OR DEVICE IS NOT IN STORAGE GROUP) |
| 4 | LINK STANDBY | LINK UNGROUPED | LINK HUB MESSAGE RECEIVED |
| 5 | LINK UNGROUPED | LINK SLAVE | LINK MASTER MESSAGE RECEIVED |
| 6 | LINK UNGROUPED | LINK MASTER | DEVICE IS IN STORAGE GROUP AND NO LINK MASTER MESSAGE RECEIVED FOR PREDETERMINED TIME |
| 7 | LINK SLAVE OR LINK MASTER | LINK SLAVE OF NEW LINK MASTER | FIRST DEVICE RECEIVES A LINK MASTER MESSAGE FROM A SECOND DEVICE AND ALL OF THE FOLLOWING ARE TRUE: 1.THE FIRST DEVICE'S LINK IS NOT SYNCHRONOUS WITH THE SECOND DEVICE'S LINK. 2.THE SECOND DEVICE IS THE LINK MASTER OF THE SECOND DEVICE'S LINK. 3.ANY OF THE FOLLOWING ARE TRUE: A.THE SECOND DEVICE'S ACTIVE STORAGE GROUP SIZE IS LARGER THAN FIRST DEVICE'S ACTIVE STORAGE GROUP SIZE. B.THE SECOND DEVICE'S ACTIVE STORAGE GROUP SIZE IS EQUAL TO THE FIRST DEVICE'S ACTIVE STORAGE GROUP SIZE AND THE SECOND DEVICE'S LINK RESOURCE IS GREATER THAN THE FIRST DEVICE'S LINK RESOURCE. C.THE SECOND DEVICE'S ACTIVE STORAGE GROUP SIZE IS EQUAL TO THE FIRST DEVICE'S ACTIVE STORAGE GROUP SIZE ... |

Fig. 10B

| | | | |
|---|---|---|---|
| 8 | LINK SLAVE | LINK UNGROUPED | ... AND THE SECOND DEVICE'S LINK RESOURCE IS EQUAL TO THE FIRST DEVICE'S LINK RESOURCE AND THE SECOND DEVICE'S LINK MASTER TIMESLOT INDEX IS LESS THAN THE FIRST DEVICE'S LINK MASTER TIMESLOT INDEX |
| 9 | LINK SLAVE | LINK MASTER | DEVICE IS NOT HUB AND NOT MEMBER OF STORAGE GROUP AND NO LINK MASTER MESSAGE RECEIVED FOR PREDETERMINED TIME |
| 10 | LINK SLAVE | LINK MASTER | ALL OF THE FOLLOWING ARE TRUE:<br>1. DEVICE IS HUB OR IS A MEMBER OF STORAGE GROUP<br>2. NO LINK MASTER MESSAGE RECEIVED FOR PREDETERMINED TIME |
| 11 | LINK SLAVE | LINK SLAVE OF NEW LINK MASTER | ALL OF THE FOLLOWING ARE TRUE:<br>1. DEVICE IS HUB OR IS A MEMBER OF STORAGE GROUP<br>2. DEVICE'S LINK RESOURCE LEVEL IS SUFFICIENTLY LARGER THAN CURRENT LINK MASTER'S LINK RESOURCE LEVEL<br>DEVICE RECEIVES A LINK MASTER MESSAGE SYNCHRONOUS WITH ITS LINK AND THE MESSAGE'S LINK RESOURCE LEVEL LARGER THAN THE DEVICE'S CURRENT LINK MASTER'S LINK RESOURCE LEVEL |
| 12 | LINK MASTER | RETIRING LINK MASTER | DEVICE RECEIVES A LINK MASTER MESSAGE SYNCHRONOUS WITH ITS LINK AND ANY OF THE FOLLOWING ARE TRUE:<br>1. THE MESSAGE'S LINK RESOURCE LEVEL IS ... |

Fig. 10C

| | | |
|---|---|---|
| | | ... LARGER THAN THE DEVICE'S LINK RESOURCE LEVEL<br>2. THE MESSAGE'S LINK RESOURCE LEVEL IS EQUAL TO THE DEVICE'S LINK RESOURCE LEVEL AND THE MESSAGE'S LINK MASTER TDMA TIMESLOT INDEX IS SMALLER THAN THE DEVICE'S LINK MASTER'S TDMA TIMESLOT INDEX |
| 13 | RETIRING LINK MASTER | LINK SLAVE | ALL OF THE FOLLOWING ARE TRUE:<br>1. DEVICE RECEIVES NO LINK SLAVE MESSAGES FROM A STORAGE GROUP DGU OR THE HUB WITH THE MESSAGE'S MASTER TIMESLOT VALUE SET TO THE DEVICE'S TIMESLOT INDEX<br>2. DEVICE HAS RECEIVED A LINK MASTER MESSAGE LESS THAN A PREDETERMINED TIME DURATION EARLIER |
| 14 | RETIRING LINK MASTER | LINK UNGROUPED | ALL OF THE FOLLOWING ARE TRUE<br>1. DEVICE RECEIVES NO LINK SLAVE MESSAGES FROM A STORAGE GROUP DGU OR THE HUB WITH THE MESSAGE'S MASTER TIMESLOT VALUE SET TO THE DEVICE'S TIMESLOT INDEX<br>2. DEVICE HAS NOT RECEIVED A LINK MASTER MESSAGE LESS THAN A PREDETERMINED TIME DURATION EARLIER |

SYSTEM AND METHOD FOR SYNCHRONIZED DISTRIBUTED DATA COLLECTION

BACKGROUND OF THE INVENTION

1. Field of the Invention

This invention generally relates to distributed unit communications and, more particularly, to a system and method for synchronizing the collection of data in a time division multiple access (TDMA) network.

2. Description of the Related Art

Data acquisition systems may be required to synchronously gather data from physically separated data generator units (DGU), each with its own internal clock, while consuming a minimal amount of power to maximize battery life and operational time. Each DGU is typically assigned a timeslot in a TDMA (time division multiple access) system so all DGUs can operate on a single physical layer resource (such as a single radio frequency).

One example of a DGU is an IMU (inertial measurement unit) attached to a user's body segments (such as the leg thigh and shank) for the purpose of measuring the RoM (range of motion) of the intervening joint (such as the knee). The IMUs must synchronously gather data so that the orientations of the body segments are measured at the same time. Measuring at different times could cause an error in calculating the relative orientation of one body segment compared to the other if both body segments are moving relative to the Earth.

Since each DGU has its own internal clock, their time bases may drift relative to each other, causing a loss of synchronization. Timing signals must be sent between the various DGUs to maintain clock synchronization. To maximize the system's battery life, timing signals should be kept to a minimum, as transmission and reception generally consume power and thus reduce system battery life.

TDMA systems typically use a single master time base generator, to which slave devices synchronize their clocks. The master device typically uses more power than the slave devices, since it needs to communicate with all slaves to maintain the synchronized communication link, while each individual slave only needs to communicate with the master, and not with the other slaves. There may be other resources, such as storage memory, which the master device consumes more quickly than slave devices.

Conventional TDMA data generator systems do not dynamically select their master device from the group of devices. They require a dedicated master device. This has the undesirable consequences of either requiring a special, separate master device, or causing the DGU acting as the master device to consume its battery more quickly than other devices and thus reduce overall system operational time.

It would be advantageous if TDMA data acquisition systems could dynamically select their master to optimize overall system operational time, and maintain system synchronization during the transition of the Link Master role from one DGU to another. Such a feature would distribute resource consumption more equally amongst the group of data generators.

SUMMARY OF THE INVENTION

Described herein is a synchronized and distributed time division multiple access (TDMA) based data collection system of Data Generating Units (DGUs) that dynamically selects its master timing and link management device (Link Master) from a group of storage capable DGUs (Storage Group) among the actively communicating Storage Group DGUs (Active Storage Group), based upon the available resources of each DGU in this Active Storage Group. Each of the system's DGUs optionally generates timestamps, and locally stores data synchronous with each of the system's other DGU's, enabling later retrieval of a synchronized data collection set collected across multiple devices, each with their own independent local clock. The system contains an optional communications hub which enables real-time data transfer to and configuration commands from other systems external to this data collection system when the hub is present. Even though the hub is not a member of the Storage Group, it is still allowed to be a Link Master. The combined plurality of DGUs and the hub constitute a plurality of communication capable devices (CCDs). Synchronization of all CCDs in the system is maintained during the transition of the Link Master role from one master capable device (MCD) to another, where an MCD is a Storage Group DGU or the hub.

Some unique aspects of the system include a synchronized, distributed, data collection system that dynamically selects its master timing and link management device from the group of MCDs based upon the available power resources (e.g., battery life) of each MCD in the group, where the MCD with the greatest available power resources becomes the master CCD, and a retiring master CCD informs its slave CCDs of the new master CCD. Storage Group DGUs can be programmatically selected, as can the number of Storage Group DGUs or the particular DGUs that are required to be in the Active Storage Group for generated data to be stored into local memory by any Storage Group DGU. Real-time data can be sent to a hub for forwarding on to an external system. The receiving capability of a DGU can be disabled during timeslots in which that DGU is not receiving a link status message or a hub message, with the selectivity dependent upon one of the following conditions: more than half of the Storage Group DGUs are communicatively linked to the master CCD, or half of the Storage Group DGUs and a Storage Group DGU with a unique identifier (UI) of greatest significance are communicatively linked to the master CCD. The DGUs are able to synchronously store data with a shared identifier that enables stored data from multiple DGUs to be time aligned when later read from storage memory.

Accordingly, a method is provided for distributed data collection synchronization. The method provides a plurality of CCDs, each CCD having consumable power resources, and the plurality of CCDs including a plurality of MCDs, not larger than the plurality of CCDs, with the plurality of MCDs including Storage Group DGUs and an optional hub. In response to each MCD evaluating its available power resources, and the MCDs comparing their availability and power resources, a master CCD (DGU) and slave DGU are determined. The slave DGUs synchronize their collection of data to a common timing reference supplied by their master CCD. One example of consumable power is battery power. With respect to the requirement of availability, a first CCD, belonging to the MCD group, may select itself as a master CCD in response to either receiving no link status message from a master CCD for a first predetermined duration of time after reset, or receiving no link status message from a master CCD for a second predetermined duration of time when the first CCD is a slave.

A slave first CCD, belonging to the MCD group, may compare its own available power resources to the available power resources of its master second CCD and select itself as the master CCD when the available power resources of the first CCD are greater than the available power resources of the second CCD by a predetermined amount. Then, the second CCD, now acting as a slave to the first CCD, synchronizes to a timing reference supplied by the master first CCD. Then, the second CCD informs a slave third CCD, previously synchronized to the second CCD's timing reference, that the first CCD is now the master of the second CCD. Similarly, if a synchronized CCD compares the available power resources of a master first CCD and a master second CCD, where a synchronized CCD is a member of a group acting in the capacity of either a master CCD or a slave CCD, the synchronized CCD selects the first CCD as its master when the available power resources of the first CCD are greater than the available resources of the second CCD.

Prior to every comparison of available power resources, the CCDs may seek affiliation with another group of CCDs. For example, if a first CCD in a first group compares the number of Active Storage Group members in the first group of CCDs to the number of Active Storage Group members in a second group, then the first CCD becomes a slave to a master in the second group when the second group has more Active Storage Group members, or when the second group has the same number of Active Storage Group members as the first group, and the available power resources of the master CCD of the second group are greater than those of the master CCD of the first group. Similarly, the first CCD becomes a slave to a second group master when the second group has the same number of Active Storage Group members as the first group, the available power resources of the master CCD of the second group are equal to those of the master CCD of the first group, and the master CCD of the second group has a unique identifier (UI) with greater significance than the UI of the master CCD of the first group. Otherwise, the first CCD remains a member of the first group.

The CCDs have assigned transmission slots in a time division multiple access (TDMA) communications system, and each slave CCD periodically receives a link status message from a master CCD, whose contents and arrival time inform the slave CCD of the current link timing from the perspective of the transmitting master CCD. The master CCD periodically receives link status messages from its slave CCDs belonging to the MCD group informing the master CCD of their link connectivity. More explicitly, a TDMA page exists including a first plurality of frames, where each frame includes a plurality of time slots. Each CCD is assigned a second plurality of Link Frames from the TDMA page in a unique frame pattern, where the second plurality is less than the first plurality. This arrangement guarantees at least one non-overlapping Link Frame per TDMA page, for each pair of CCDs, independent of any time alignment of TDMA page overlapping.

Thus, when a first CCD is a slave, it transmits link status messages only in the first CCD's assigned transmission slot during the assigned link frames of the first CCD's master. When the first CCD is a master, the first CCD transmits link status messages only during its assigned transmission slot of its assigned link frames. When the first CCD is a retiring master, the first CCD transmits link status messages only during its assigned transmission slot of both the assigned link frames of the first CCD's master and the assigned link frames of the first CCD itself.

DGUs are able to selectively disable their receivers in response to being a member of a dominant group of synchronized DGUs, where a dominant group includes either more than half the number of Storage Group DGUs, or half the number of Storage Group DGUs and the Storage Group DGU with the most significant UI. Thus, when a first DGU is a slave in a dominant group, it enables its receiver to receive link status messages during the transmission slot of the first DGU's master CCD in the master CCD's Link Frames. When the first DGU is a master in a dominant group, it enables its receiver to receive link status messages during the transmission slots of the first DGU's slave CCDs, belonging to the MCD group, in the first DGU's Link Frames. When the first DGU is a retiring master in a dominant group, it enables its receiver to receive link status messages during both the transmission slot of the first DGU's master CCD in its master CCD's Link Frames, and the transmission slots of the first DGUs slave CCDs, belonging to the MCD group, in the first DGU's Link Frames. The hub enables its receiver whenever it is not transmitting, so that it may receive link status and data messages from all DGUs, whether or not they are in the Storage Group.

Storage Group DGUs only store data when the plurality of communicating DGUs are part of a group made up of a minimum number of synchronized Storage Group DGUs, or when the group is made up of a required subset of synchronized Storage Group DGUs, or when the group is made up of both a minimum number of synchronized Storage Group DGUs and a required subset of synchronized Storage Group DGUs. In one aspect, Storage Group slave DGUs, master DGUs, and retiring master DGUs all periodically synchronously store a shared identifier uniquely indicating the time alignment of distributed stored data.

Additional details of the above-described method and a system for the synchronized collection of data are provided below.

BRIEF DESCRIPTION OF THE DRAWINGS

FIG. 1A is a schematic block diagram of a system for distributed data collection synchronization.

FIG. 1B is a Venn diagram showing the group relationships between communication capable device types.

FIGS. 4A through 4C respectively depict three examples of DGU applications referenced herein to provide greater clarity of system features.

FIG. 5 depicts the message types used in the system and enumerates their contents.

FIGS. 10A-10C present a table of the state transition rules.

DETAILED DESCRIPTION

Figure 2:
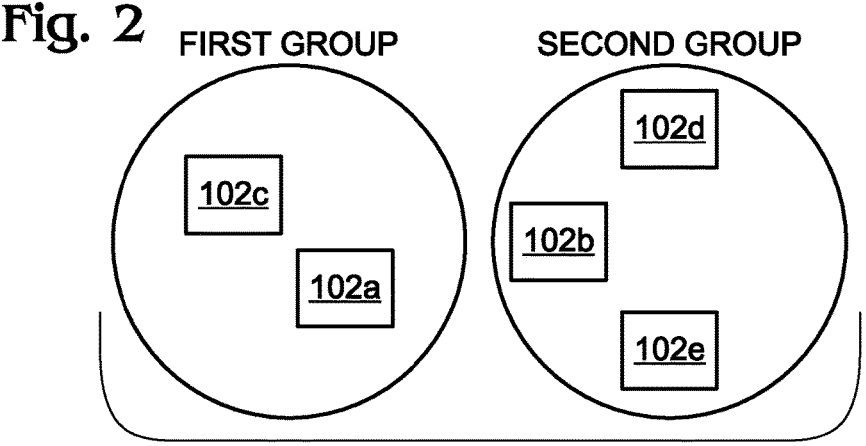
FIG. 2 is a schematic block diagram depicting additional details of the system shown in FIG. 1A.

The systems and methods described herein use the notation, concepts, and techniques described in the following applications, which are incorporated herein by reference:

Serial No. 15/155,943, entitled, SYSTEM AND METHOD FOR MEASURING BODY JOINT RANGE OF MOTION, filed May 16, 2016;

Ser. No. 15/091,869, entitled, SYSTEM AND METHOD FOR DETERMINING ORIENTATION OF BODY SEGMENTS USING INERTIAL MEASUREMENT UNITS, filed Apr. 6, 2016;

Ser. No. 14/873,946, entitled, SYSTEM AND METHOD FOR DETERMINING THE ORIENTATION OF AN INERTIAL MEASUREMENT UNIT (IMU), filed Oct. 2, 2015; and, Serial No. 14/742,852, SENSOR CALIBRATION METHOD AND SYSTEM, filed Jun. 18, 2015.

FIG. 1A is a schematic block diagram of a system for distributed data collection synchronization. The system 100 comprises a plurality of five synchronized communication capable devices (CCDs). A synchronized CCD is defined herein as a member of a group acting in the capacity of either a master CCD (also referred to herein as a Link Master) or a slave CCD (also referred to herein as a Link Slave), communicatively synchronized with a time base common to all members of the group, supplied by the master CCD. The plurality includes four data generation units (DGUs) all sharing a common reference designator 102, and one optional hub 103. Specific DGUs are differentiated by unique suffix letter, such as first DGU 102a, second DGU 102b, third DGU 102c, and fourth DGU 102d. In this example, first DGU 102a, second DGU 102b, and third DGU 102c are all capable of storing data, and therefore are Storage Group DGUs. Since Storage Group DGUs 102a, 102b, and 102c are communicatively synchronized, they are also Active Storage DGUs. DGU 102d is not capable of storing data, and therefore is a non-Storage Group DGU. The Storage Group DGUs 102a, 102b, and 102c, and the hub 103 are all capable of becoming a master CCD, and therefore are master capable devices (MCDs). Non-Storage Group DGUs, such as DGU 102d are not permitted to become a master CCD and therefore are not MCDs.

FIG. 1B shows the group relationships between CCDs, DGUs, Non-Storage Group DGUs, Storage Group DGUs, Active Storage Group DGUs, MCDs, and the hub.

Returning to FIG. 1A and using first DGU 102a as an example, each CCD (DGU or hub) comprises a processor 104, a non-transitory memory 106, a transmitter and receiver (shown as transceiver or radio 108), a consumable power resource 110, and a unique identifier (UI) 112. Here, the transceiver 108 is shown to be wireless, enabled with antenna 113, but other modes of communication are possible. A consumable power resource may be a battery with a limited supply of exhaustible power. A synchronization application 114 is enabled as a sequence of processor executable steps and stored in the memory 106. The synchronization application 114 evaluates the availability of MCDs and their consumable power, and selects the CCD's master CCD in response to the evaluation. A CCD considers another CCD to be available if the other CCD is an MCD, and it synchronously communicates with the other CCD. A slave Storage Group DGU synchronizes its collection of data, for both sampling time and storage in the memory 106, to a common timing reference supplied by its master CCD.

With respect to the issue of availability, any MCD (for example, DGU 102a) can select itself as a master CCD in response to either receiving no link status message from a master CCD for a first predetermined duration of time after reset, or receiving no link status message from a master CCD for a second predetermined duration of time when the MCD is a slave. In contrast, any CCD not in the MCD group (for example, DGU 102d) can never select itself as a master CCD.

With respect to the comparison of power resources, any slave CCD belonging to the MCD group, may compare its own available power resources to the available power resources of its master CCD, and select itself as a master CCD when the available power resources of the slave CCD are greater than the available power resources of its master CCD by a predetermined amount. For example, the first DGU 102a, in the capacity of a slave CCD to the second DGU 102b and belonging to the MCD group, may compare its available power resources to DGU 102b and select itself as a master CCD when those resources are greater than the resources of second DGU 102b by a predetermined amount. Then, the second DGU 102b, initially acting as a master CCD, compares its available power resources to now master first DGU 102a, and if it determines that first DGU 102a has greater power resources, the second DGU 102b becomes a slave to first DGU 102a and synchronizes to a timing reference supplied by the master first DGU 102a.

When a master second CCD becomes a slave to a master first CCD, the second CCD informs the second CCD's slave CCDs of the new master first CCD by first transitioning to a retiring master. When all of the retiring master second CCD's slave CCDs, belonging to the MCD group, no longer communicate with the retiring master second CCD for a predetermined time, then the retiring master second CCD completes the transition to a slave CCD of the master first CCD. Continuing the previous example, when second DGU 102b takes first DGU 102a as its master, second DGU 102b first becomes a retiring master to inform third DGU 102c, which was a slave of second DGU 102b, of the second DGU 102b's new master first DGU 102a. When now retiring master second DGU 102b no longer receives status messages from third DGU 102c. Then, retiring master second DGU 102b completes its transition to a slave of master first DGU 102a. Even though the fourth DGU 102d had the second DGU 102b as its master, retiring master second DGU 102b does not wait for a lack of status messages from the fourth DGU 102d, because the fourth DGU 102d is not an MCD, since it is not in the Storage Group.

A DGU may further comprise a sensor 116 to collect data 118 from the environment, with the data being stored in memory 106. The optional hub is not required to contain a sensor device, since the hub does not collect data. The various components of a CCD may be connected via bus 120. Generally, the CCD may be considered as a type of computer device, the workings of which are well understood in the art. The items in memory 106 may be referred to as a computer-readable medium. As used herein, the term "computer-readable medium" refers to any medium that participates in providing instructions to a processor for execution or the storage of information. Such a medium may take many forms, including but not limited to, non-volatile media, volatile media, and transmission media. Non-volatile media includes, for example, optical or magnetic disks. Volatile media includes dynamic memory. Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, or any other memory chip or cartridge.

FIG. 2 is a schematic block diagram depicting additional details of the system shown in FIG. 1A. Two exemplary groups of CCDs are shown. The first CCD 102*a* is the master of a first group of Active Storage Group DGUs including slave DGU 102*c*, all communicatively synchronized with the first group's master CCD 102*a*. The second CCD 102*b* is the master of a second group of Active Storage Group CCDs including slave CCDs 102*d* and 102*e*, all communicatively synchronized with the second group's master CCD 102*b*. The first and second groups are not communicatively synchronized with each other. In one aspect, each CCD seeks affiliation with another group of CCDs prior to every evaluation of CCD availability and consumable power in its current group of CCDs. For example, a CCD in a first group, either CCD 102*a* or 102*c*, compares the number of Active Storage Group members in the first group to the number of Active Storage Group members in a second group, and becomes a slave to the master second CCD 102*b* in the second group in response to the second group having more Active Storage Group members (as shown). Alternatively but not shown, a CCD in the first group may become a slave to second CCD 102*b* if the second group has the same number of Active Storage Group members as the first group, and the available power resources of the master second CCD 102*b* of the second group are greater than those of the master first CCD 102*a* of the first group. As another alternative not shown, a CCD in the first group may become a slave to second CCD 102*b* if the second group has the same number of Active Storage Group members as the first group, the available power resources of the master second CCD 102*b* of the second group are equal to those of the master first CCD 102*a* of the first group, and the master second CCD 102*b* of the second group has a UI with a greater significance than the UI of the first master CCD 102*a* of the first group. Some examples of a UI with greater significance include the lowest numbered UI, the highest numbered UI, and a particular UI numbered designated as having high priority.

As described in more detail below, see FIG. 6, each CCD 102 is assigned a transmission slot from a frame of timeslots in a time division multiple access (TDMA) communications system, where each frame includes a plurality of time slots. As such, each slave CCD periodically receives a link status message from a master CCD, whose contents and arrival time inform the slave CCD of the current link timing from the perspective of the transmitting master CCD. The master CCD periodically receives link status messages from its slave CCDs, belonging to the MCD group, informing the master CCD of their link connectivity.

Figure 11:
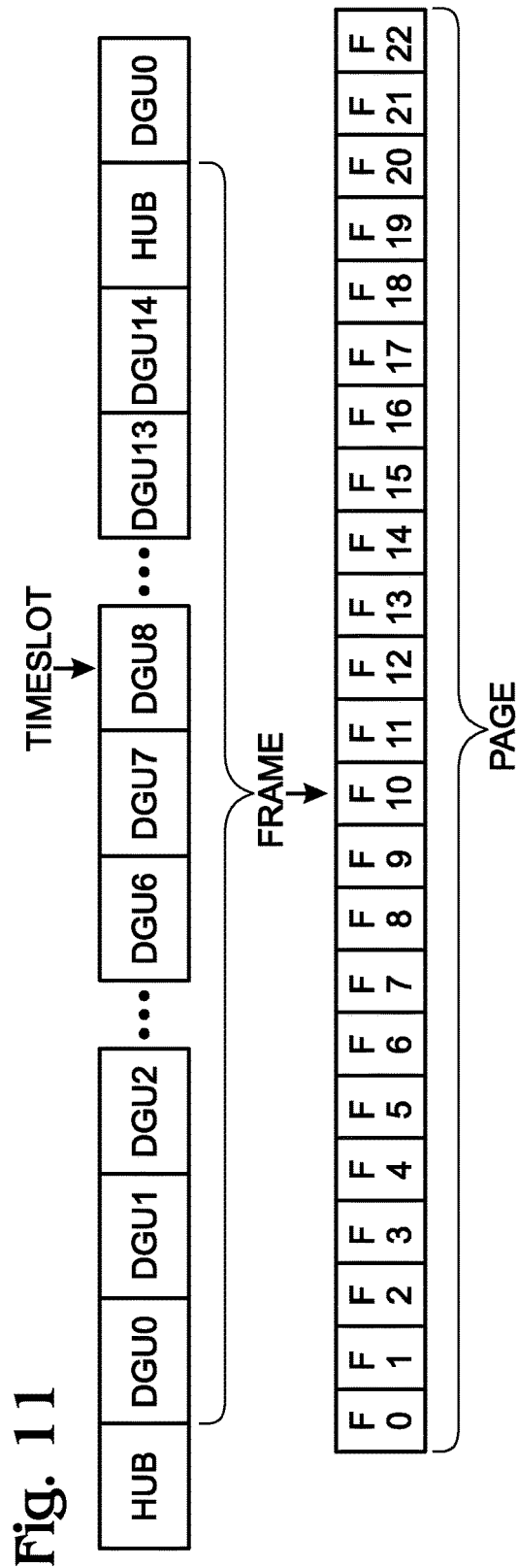
FIG. 11 depicts an exemplary TDMA page structure, where each TDMA frame is 16 timeslots long and the TDMA page is 23 frames long.

As shown in FIG. 11, a first plurality of frames is grouped into a TDMA page. Each CCD is also assigned a second plurality of link frames from the TDMA page in a unique frame pattern, where the second plurality is less than the first plurality, guaranteeing for each pair of CCDs at least one non-overlapping master link status transmission frame per TDMA page, independent of any time alignment of TDMA page overlapping, see FIG. 12.

Returning to FIG. 1A, if the first CCD 102*a* is acting as a slave CCD (to second CCD 102*b* for example), the first CCD transmits link status messages only during its assigned transmission slot of the assigned link frames of first CCD's master. If the first CCD 102*a* is acting as a master CCD, the first CCD transmits link status messages only during its assigned transmission slot of the assigned link frames of the first CCD itself. If the first CCD 102*a* is acting as a retiring master CCD, the first CCD transmits link status messages only during its assigned transmission slot of both the assigned link frames of the first CCD's (new) master and the assigned link frames of the first CCD itself.

Generally, the DGUs 102 are able to selectively disable their receivers in response to being a member of a dominant group of communicatively synchronized DGUs, where a dominant group includes more than half the number of Storage Group DGUs, or half the number of Storage Group DGUs and the Storage Group DGU with the most significant UI. If a DGU is a member of a non-dominant group, a DGU enables its receiver whenever it is not transmitting. The hub enables its receiver whenever it is not transmitting, so that it may receive link status and data messages from all DGUs, whether or not they are in the Storage Group.

More explicitly, if the first DGU is a slave in a dominant group, it only enables its receiver to receive link status messages during the transmission slot of the first DGU's master CCD in the master CCD's Link Frames. If the first DGU is a master in a dominant group, it only enables its receiver to receive link status messages during the transmission slots of the first DGU's slave CCDs, belonging to the MCD group, in the first DGU's Link Frames. If the first DGU is a retiring master in a dominant group, it only enables its receiver to receive link status messages during both the transmission slot of the first DGU's master CCD in its master CCD's Link Frames, and the transmission slots of the first DGUs slave CCDs, belonging to the MCD group, in the first DGU's Link Frames.

In another aspect it is noted that not all communicating DGUs 102 necessarily store data. The communicating DGUs 102 only store data when they comprise a minimum number of synchronized Storage Group DGUs (i.e., the minimum number required to make the data meaningful), a required subset of synchronized Storage Group DGUs (usually related by proximity), or both a minimum number of synchronized Storage Group DGUs and a required subset of synchronized Storage Group DGUs. Storage Group slave DGUs, master DGUs, and retiring master DGUs may all periodically synchronously store a shared identifier uniquely indicating the time alignment of distributed stored data.

The above system describes a synchronized and distributed TDMA based data collection system of DGUs that dynamically selects its master timing and link management device (Link Master) from a group of storage enabled DGUs (Storage Group) among the actively communicating Storage Group DGUs (Active Storage Group) based upon the available resources of each DGU in this Active Storage Group. Each of the system's DGUs optionally generates timestamps, and locally stores data synchronous with each of the system's other DGU's, enabling later retrieval of a synchronized data collection set collected across multiple devices, each with their own independent local clock. A subset of the Storage Group DGUs can be optionally required to be active for data storage to be active in any of the Storage Group DGUs. This subset is called the Required Group. Also optionally, a minimum number of Active Storage Group members may be required for data storage to be active (Active Storage Threshold). The system contains an optional communications hub which enables real-time data transfer to and configuration commands from other systems external to this data collection system when the hub is present. Even though the hub is not a member of the Storage Group, it is still allowed to be a Link Master. The combined plurality of DGUs and the hub constitute a plurality of communication capable devices (CCDs). Synchronization of all CCDs in the system is maintained during the transition of the Link Master role from one master capable device (MCD) to another, where an MCD is a Storage Group DGU or the hub.

Each DGU contains a local power source, processor, data generator, communication interface, and optionally local data storage memory. Each of these elements is application specific. Example power sources are battery and gasoline. Example data generators are inertial measurement unit (IMU), digital thermometer, and digital barometer. Example communication interfaces are radio, I2C, and UART. In one aspect, IMU sensors measure the orientation of human body segments relative to Earth.

Figure 3:
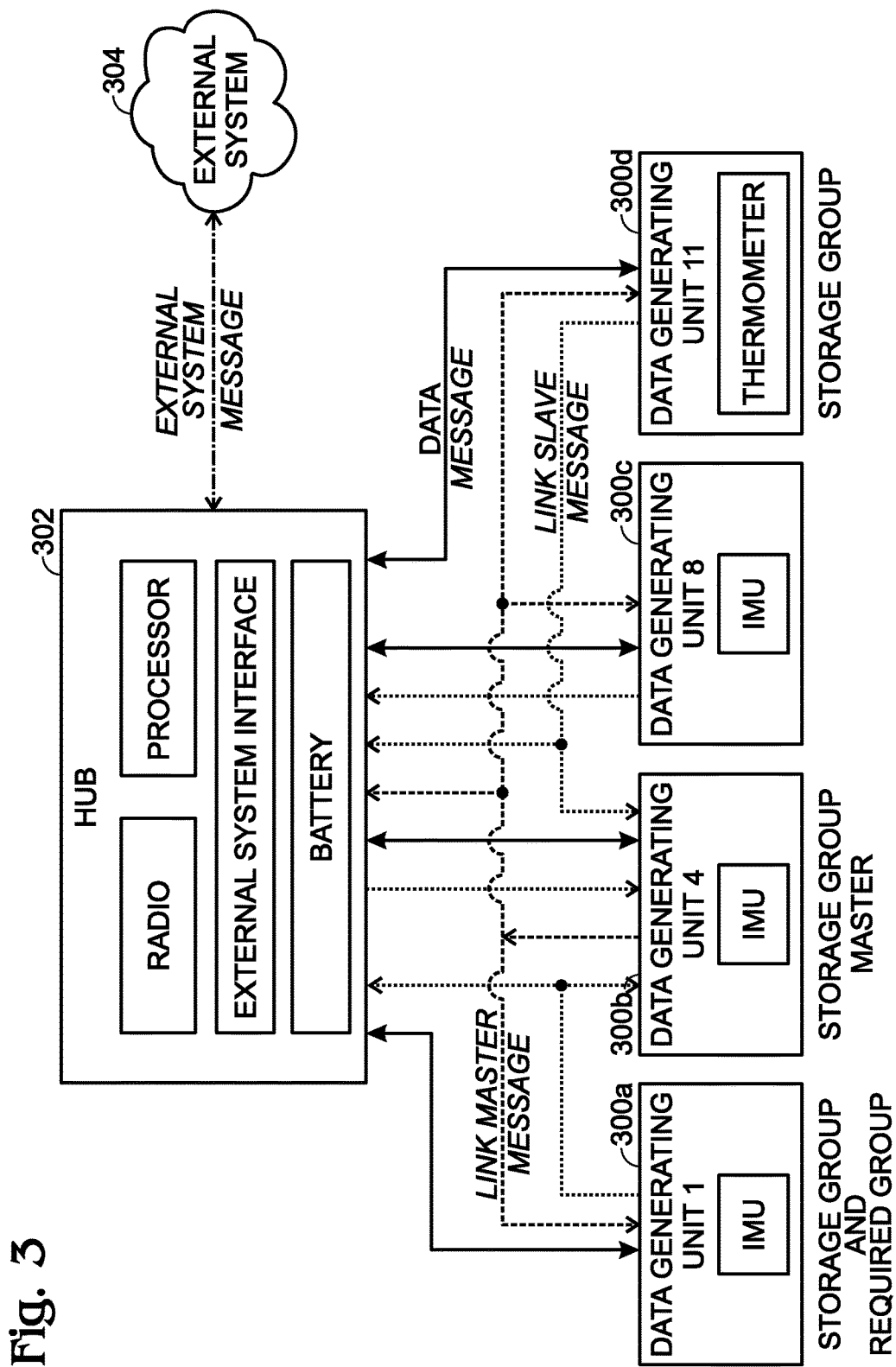
FIG. 3 is a schematic block diagram showing an exemplary data collection system consisting of four DGUs and a hub connected to an external system using any desired interface.

FIG. 3 is a schematic block diagram showing an exemplary data collection system consisting of four DGUs 300a, 300b, 300c, and 300d, and a hub 302 connected to an external system 304 using any desired interface. In this example, three of the DGUs generate data with an IMU and the fourth one uses a digital thermometer. Other types of sensors are also possible.

Figure 4A:
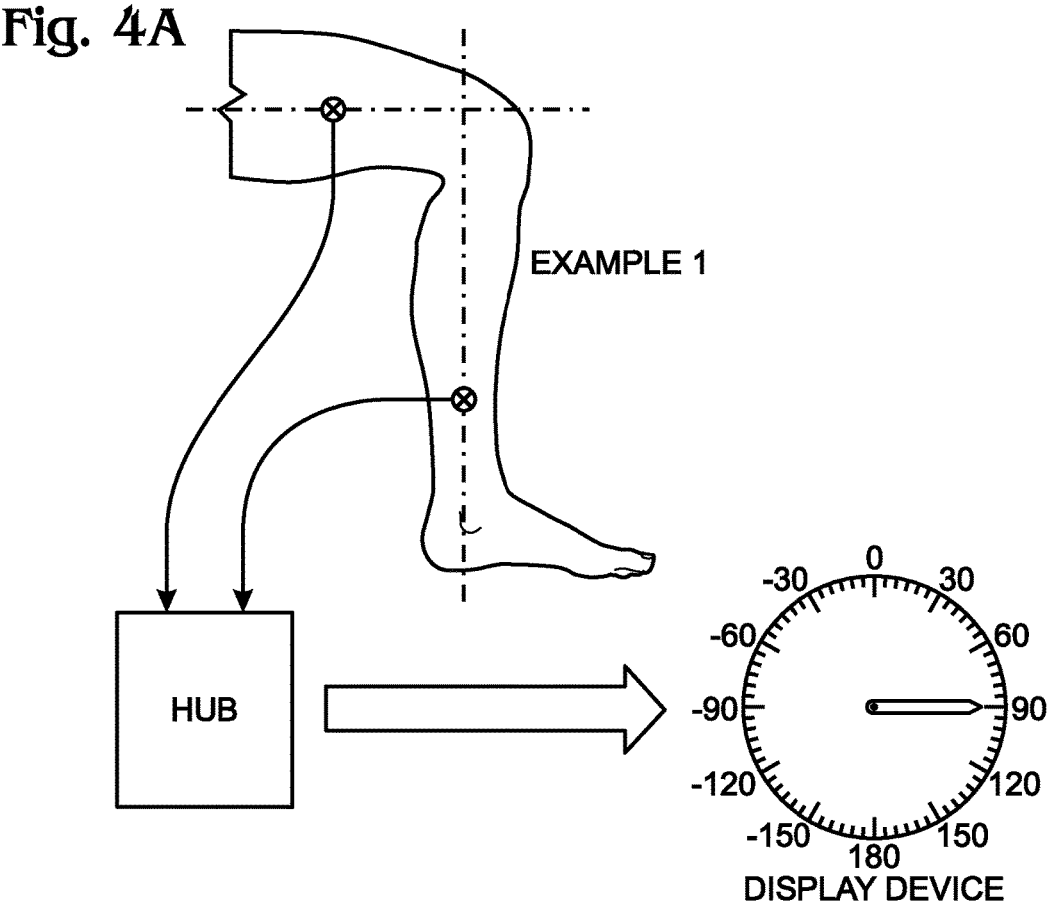

FIGS. 4A through 4C respectively depict three examples of DGU applications referenced herein to provide greater clarity of system features. All three examples focus on range of motion (RoM) measurements for human body joints, specifically the knee and foot. Parent application Ser. No. 15/155,943 describes in detail how RoM is calculated from orientation measurements. While these examples focus on RoM, the system described herein can also be used for other applications requiring synchronized data storage with distributed, power constrained systems, such as synchronously measuring temperature or barometric pressure at opposite sides of a building.

The first exemplary application (FIG. 4A) is real-time measurement of a knee's RoM with visual feedback to the user. In this case, DGUs incorporating orientation sensors are placed on the user's thigh and shank. The DGUs transmit real-time orientation data to a hub, which then forwards the data on to a display device. In this example, none of the DGUs are in the Storage Group. Data is not stored in any DGU, and is only streamed real-time to the hub for viewing by the user while the hub is present. The hub is the only device that can be the Link Master, since none of the DGUs are in the Storage Group.

The second exemplary application (FIG. 4B) is ambulatory measurement of a knee's RoM, with data being gathered during a user's normal day and then being downloaded and viewed later. Again, DGUs incorporating orientation sensors are placed on the user's thigh and shank. However, in this case, a hub is not used, since real-time viewing is not required. Therefore, the DGUs do not stream real-time data and instead only exchange link management messages, reducing overall power consumption and increasing battery life relative to the live streaming condition. Since data is required from both DGUs in order to calculate RoM, both DGUs are configured to be in the Storage Group and in the Required Group, causing data to be stored in any DGU only when both DGUs are active. This keeps the DGUs memory from being filled with unusable data when only one DGU is active. If a hub is activated, then real-time streaming does begin. However, data storage is not interrupted by streaming, so stored data remains continuous and independent of streaming status.

The third exemplary application (FIG. 4C) is ambulatory measurement of both a knee's and an ankle's RoM, with data being gathered during a user's normal day and then being downloaded and viewed later. DGUs incorporating orientation sensors are placed on the user's thigh, shank, and foot. A hub is not used, since real-time viewing is not required. Again, DGUs do not stream real-time data and instead only exchange link management messages, reducing overall power consumption and increasing battery life relative to the live streaming condition. Measuring knee RoM requires data from the shank and thigh DGUs, but not the foot DGU. Measuring ankle RoM requires data from the shank and foot DGUs, but not the thigh DGU. Therefore, measuring at least one of the two joints requires the shank DGU and at least one of the other two DGUs to be active, for a total of at least two DGUs to be active. So, the system would be configured with all three DGUs in the Storage Group, only the thigh DGU in the Required Group, and the Active Storage Threshold set to two. Again, if a hub is activated, then real-time streaming does begin. However, data storage is not interrupted by streaming, so stored data remains continuous and independent of streaming status.

In general, a system consists of at least one DGU. The maximum number of DGUs is only limited by the bandwidth of the communication medium carrying signals between the devices. Only DGUs in the Storage Group can store data in their internal memory. DGUs can be programmatically configured in and out of the Storage Group by selectively sending storage enable and disable configuration messages originated by the external system to the DGUs via the hub, adding and removing individual DGUs to and from the Storage Group. Alternatively, the DGUs can be permanently added or removed from the Storage Group at manufacturing time to remove the need for a hub to perform this function.

If a DGU is not in the Storage Group, it does not store data in its local memory; however, it can still send real-time data to the hub when the hub is present. The first exemplary application in FIG. 4A is an example of this condition.

As described earlier, data storage can be controlled by a number of methods. The first method is to: set the Active Storage Threshold to the minimum required size of the Active Storage Group for storage to occur, start storing data once the Active Storage Group size meets that threshold, and stop storing data when it goes below that threshold. Setting the Active Storage Threshold to the value of one causes a Storage Group DGU to store data without being communicatively linked to any other DGU.

The second data storage control method is to: include at least one DGU in the Required Group, start storing data once all DGUs in the Required Group are active, and stop storing data when at least one DGU in the Required Group is not active. The second exemplary application of FIG. 4B is an example of this condition.

The third data storage control method is a hybrid of the first two, where the Active Storage Threshold is greater than one and the Required Group contains at least one DGU. Then storage is only active when both conditions are true. The third exemplary application of FIG. 4C is an example of this condition.

FIG. 5 depicts the message types used in the system and enumerates their contents. The use of each message field is described in further detail below. Link Master and Link Slave Messages travel between each DGU to synchronize data collection. When the hub is present, it also sends and receives these link messages to maintain synchronization with the system. The hub may also receive Data Messages from the DGUs to forward on to an external system, and may forward external data messages received from an external system onto any or all of the connected DGUs. In the first exemplary application of FIG. 4A, the display device is an example of an external system receiving data.

Figure 6:
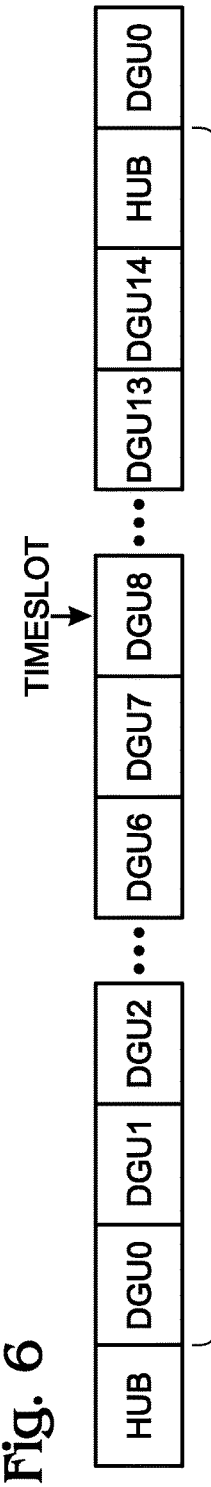
FIG. 6 depicts an exemplary TDMA frame with 15 DGU timeslots and 1 hub timeslot.

FIG. 6 depicts an exemplary TDMA frame with 15 DGU timeslots and 1 hub timeslot. Messages are sent between the system's CCDs using a TDMA framework. Each CCD is assigned a dedicated timeslot in a TDMA frame during which it can transmit. A DGU's transmit timeslot may be programmatically assigned via a message from the hub or the external system, or be permanently assigned during device manufacturing. The hub is assigned a predetermined timeslot. Therefore, the maximum number of DGUs that a TDMA frame supports is equal to the number of TDMA timeslots minus one. A CCD is not allowed to transmit outside of its assigned timeslot. CCDs selectively enable their receivers in other CCDs' timeslots to receive link status messages and synchronize timing. The hub additionally receives Data Messages from DGUs.

Some systems may have fewer DGUs than the system has timeslots. For example, the TDMA frame shown in FIG. 6 supports 15 DGUs, but the system shown in FIG. 3 only contains 4 DGUs. In this case, the system would only use 4 of the 15 available DGU timeslots.

Some systems may have a Storage Group with fewer DGUs than the system has timeslots. For example, in the system shown in FIG. 3, the external system might request DGUs 300a, 300b, and 300d to store data but not request DGU 300c to store data. In this case, the Storage Group only consists of DGUs 300a, 300b, and 300d. As described above, having a DGU be active but not be in the Storage Group still allows that DGU to send real-time data to the hub and the external system. The first exemplary application of FIG. 4A requires no members to be in the Storage Group, since the example only uses real-time streaming.

Some systems may have a Required Group with fewer DGUs than the Storage Group. For example, in the system shown in FIG. 3, the external system might only request DGU 300a to be required, and not request DGUs 300b or 300d to be required. In this case, the Required Group only consists of DGU 300a. As described above, having a Required Group that is smaller than its associated Storage Group ensures that DGUs critical to a particular application are active during data storage. The third exemplary application of FIG. 4C is an example of this usage.

System synchronization is maintained by designating a single CCD, belonging to the MCD group, to be the current Link Master, and having all other devices adjust their timing to match the timing of the Link Master Messages that they receive from the Link Master. The Link Master in turn receives messages from the other CCDs, belonging to the MCD group, to determine current link connectivity status. It then reports this status to the other devices via its Link Master Message. By receiving link messages only from other MCD members, the Link Master reduces its power consumption, relative to attempting to receive link messages during all TDMA frame timeslots. In the system of FIG. 3, since DGU 300c is not in the Storage Group, the example Link Master, DGU 300b, can disable its radio during the DGU 300c timeslot.

Figure 7:
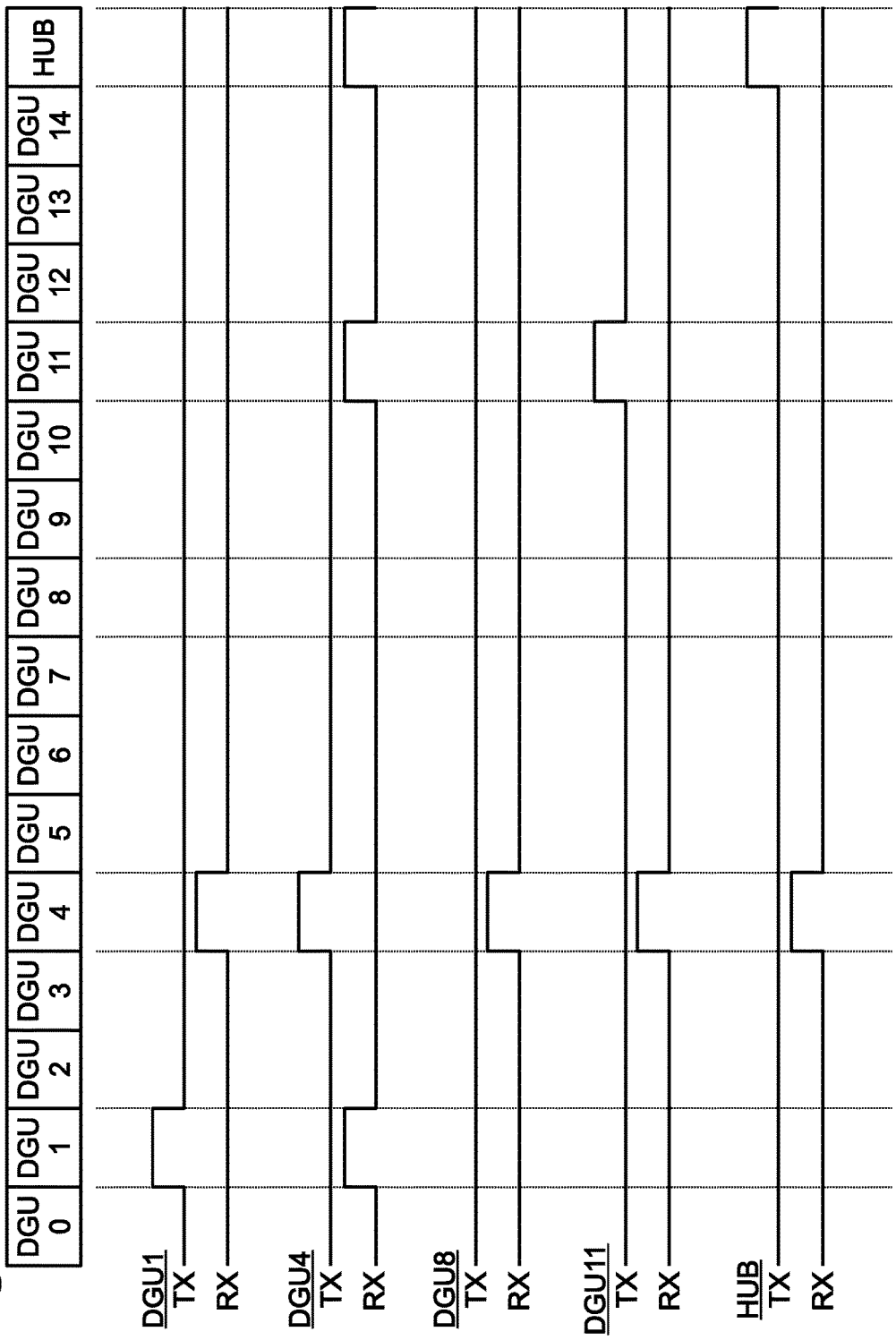
FIG. 7 depicts the link status message timing for the exemplary system of FIG. 3, where DGU 300a through 300d are assigned timeslots 1, 4, 8, and 11, respectively.

FIG. 7 depicts the link status message timing for the exemplary system of FIG. 3, where DGU 300a through 300d are assigned timeslots 1, 4, 8, and 11, respectively. The Link Master (DGU 300b) transmits a Link Master Message during its own timeslot. All other DGUs (300a, 300c, and 300d) and the hub receive that message during the Link Master's timeslot. Also, all other DGUs and the hub transmit Link Slave Messages during their own individual timeslots. The Link Master (DGU 300b) receives the subset of those Link Slave Messages that were transmitted by CCDs belonging to the MCD group during those slave timeslots. DGU 300c, which is not in the Storage Group, transmits Link Slave Messages, but they are not received by DGU Link Masters. They are only received by the hub 302, which keeps its receiver enabled whenever it is not transmitting.

Figure 8:
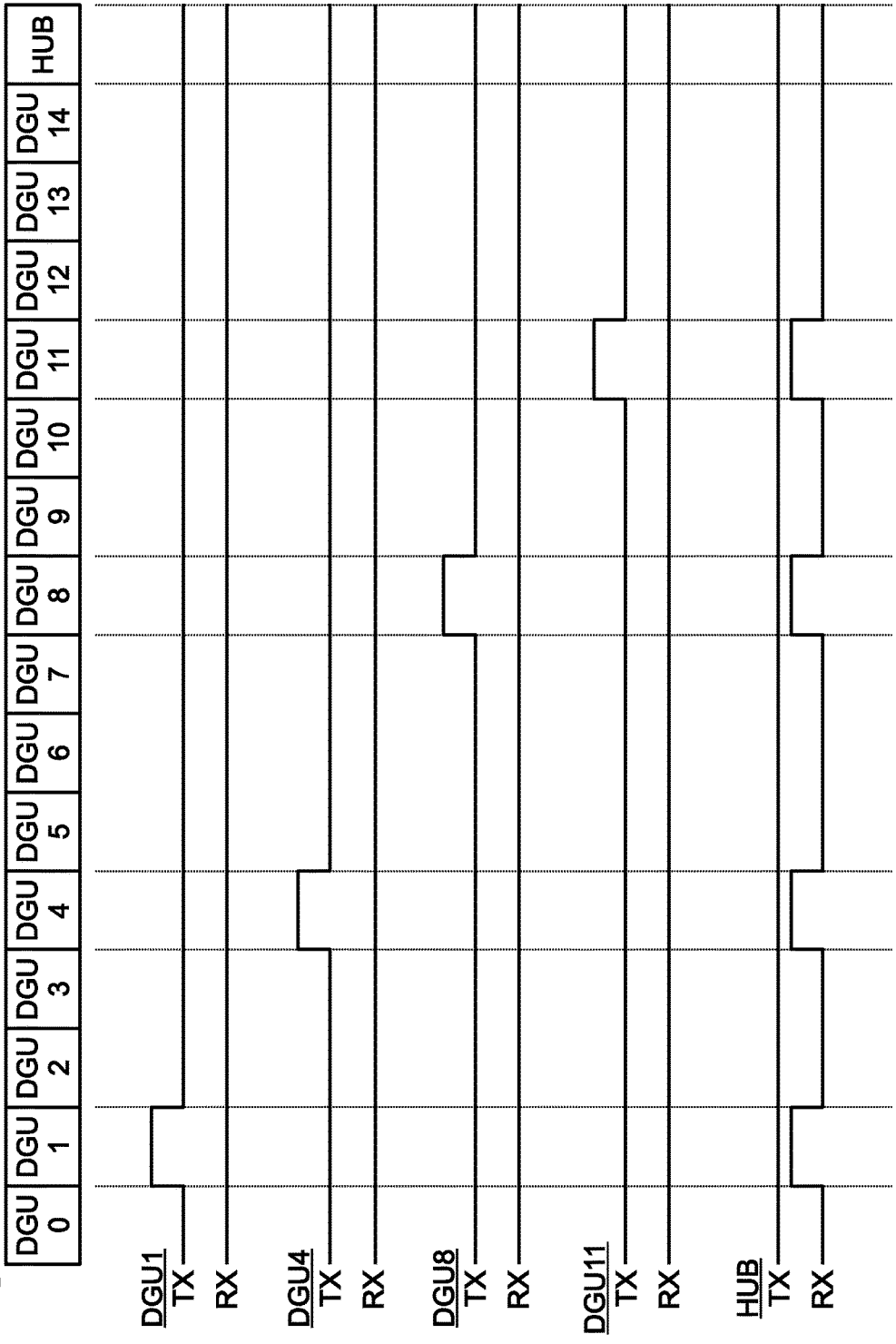
FIG. 8 depicts the data message timing for the exemplary system of FIG. 3.

FIG. 8 depicts the data message timing for the exemplary system of FIG. 3. The hub receives data messages from all DGUs, enabling generated data to travel from a DGU to the hub and then be forwarded on to an external system. The hub additionally sends Link Hub Messages to DGUs that do not yet have an assigned timeslot, enabling them to receive a timeslot assignment via a command originated by the hub or the external system. All DGUs can transmit data in their own timeslots, independent of whether they are in the Storage Group. The hub receives data from the DGUs in those timeslots.

DGUs can transmit Data Messages to the hub in their assigned timeslot in any TDMA frame when the hub is active. The Link Master receives link messages from the hub and therefore can detect if the hub is active. The Hub Active field of the Link Master Message informs Link Slaves if the hub is active. For timeslots that include both link and data messages, Data Messages are sent after link messages. This facilitates system timing synchronization based upon link message arrival timing. Data Messages are identifiable by a message type header field present in all messages sent across the link. They also contain a Device Timeslot field identifying the message sender, a sequence number that enables data transmission to be retried if the message is not acknowledged by the hub, and a data payload that is application specific.

Devices use a link resource parameter in the Link Master Message to determine if they should request to become the new Link Master. Link resources are those resources which are required to maintain the link, such as battery power. During Link Master state transitions, the system may temporarily have multiple Link Masters.

Figure 9:
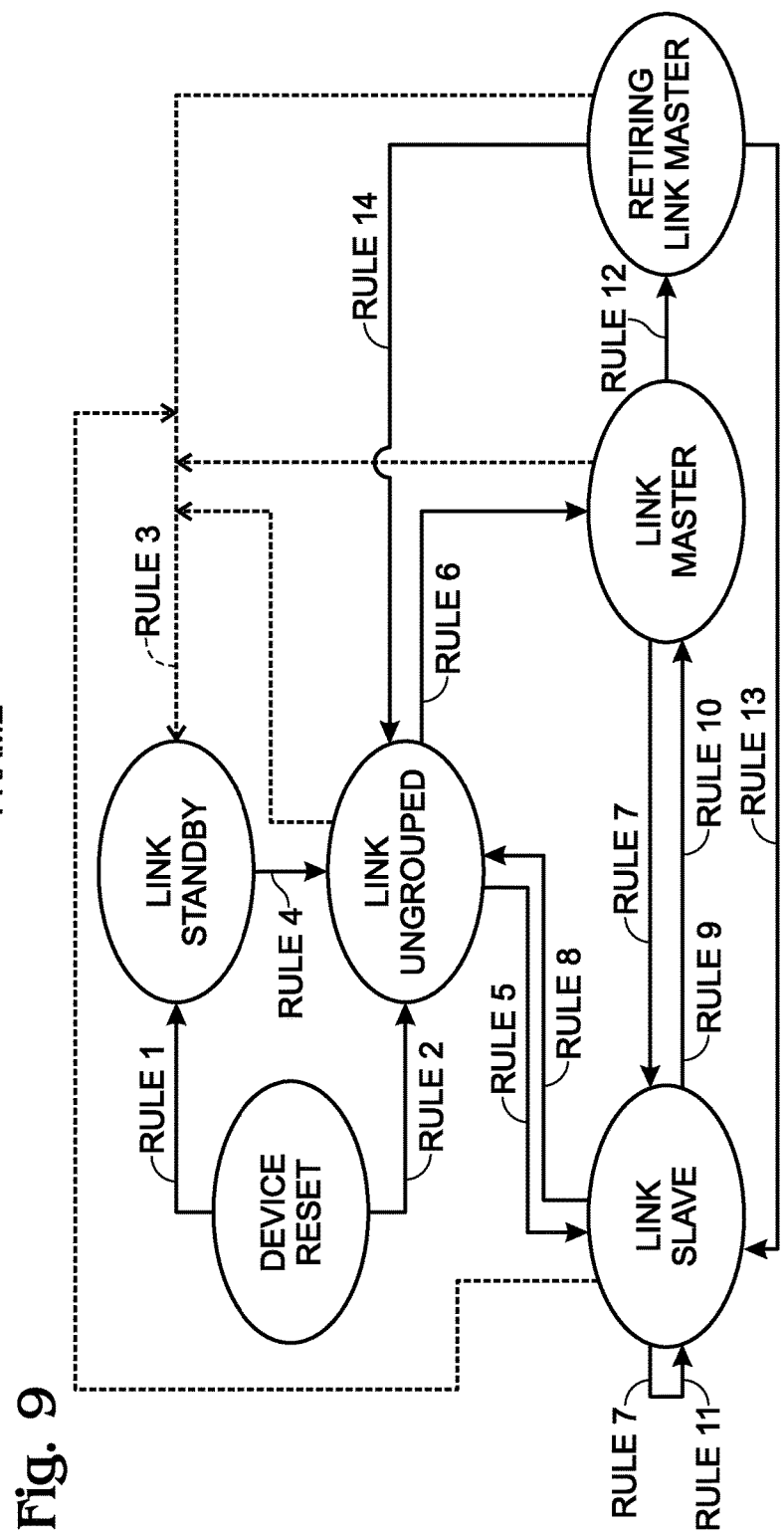
FIG. 9 is a diagram depicting the transitions between CCD link states.

FIG. 9 is a diagram depicting the transitions between CCD link states, and FIGS. 10A-10C present a table of the state transition rules. When a CCD is reset, it transitions to the Link Standby state if it does not yet have a timeslot assignment or is not in the Storage Group (Rule 1). Otherwise, it transitions to the Link Ungrouped state (Rule 2). Similarly, independent of a CCD's state, if a Link Hub Message is not received during a predetermined time duration (such as the time required to for a Link Master to send 6 Link Master Messages), then a CCD transitions to the Link Standby state if the CCD does not yet have a timeslot assignment, or is not in the Storage Group (Rule 3). This can greatly increase battery life by allowing the CCD to disable its receiver for multiple frame times when no hub is present, if that CCD is only used for real-time data streaming and not for data storage.

When a CCD is in the Link Standby state, it periodically attempts to receive a Link Hub Message from the hub. If it does receive a Link Hub Message, then the CCD transitions to the Link Ungrouped state (Rule 4).

When a CCD is in the Link Ungrouped state, it searches for a Link Master by attempting to receive a Link Master Message. If the CCD receives a Link Master Message, then it becomes a Link Slave (Rule 5). If it does not receive a Link Master Message within a predetermined amount of time (such as the time required to for a Link Master to send 6 Link Master Messages) and it is part of the Storage Group, then it becomes a Link Master (Rule 6).

Link Master Messages are identified by the message type header field. They also contain a Device Timeslot field identifying the message sender and a Master Timeslot field identifying the CCD that the sender uses as its current Link Master. When a CCD in the Link Ungrouped state receives a Link Master Message, it uses the Device Timeslot field to set its link timing and the Master Timeslot field to set its current Link Master.

DGUs that do not yet have an assigned timeslot cannot be part of the Storage Group, and therefore also cannot become the Link Master. In order to receive a timeslot assignment, they communicate with the hub during the hub timeslot by responding to Link Hub Messages sent by the hub. The hub in turn assigns the DGU a timeslot or sends a message to the external system informing the external system that an unassigned DGU is available for assignment. The external system can then send a timeslot assignment message to the hub which is then forwarded on to the unassigned DGU in the Link Hub Message to assign the DGU to the requested timeslot. Alternatively, all DGUs can have their timeslots predetermined and permanently set at manufacturing time, avoiding the need for a hub to configure DGU timeslots.

When a CCD is in the Link Master state, it periodically transmits a Link Master Message to inform the other devices of the link timing and status. If two or more CCDs are relatively simultaneously turned on, while all other CCDs remain off, the on CCDs may relatively simultaneously transition from the Link Ungrouped state to the Link Master state and then simultaneously transmit Link Master Messages. Since the CCDs are simultaneously transmitting, they might not receive each other's Link Master Messages, and therefore a link might not be established between the CCDs.

To avoid this condition, TDMA frames are grouped into TDMA pages, and Link Masters only transmit Link Master Messages during their assigned Link Frames in a TDMA page. Similarly, Link Slaves only transmit Link Slave Messages during their own timeslot in their current Link Master's Link Frames. This enables Link Masters to determine which CCDs are in the Active Storage Group.

Link frame assignment is unique to each device, similar to how timeslot assignment is unique. The minimum number of TDMA frames in a TDMA page is dependent upon the number of timeslots in a TDMA frame, such that for any given two CCDs, each CCD has a time during a TDMA page to transmit when the other CCD is not transmitting, independent of when the devices were actually turned on. This is accomplished by spacing the Link Frames in a TDMA page for any given CCD rotationally incommensurate with the Link Frame spacing of all other DGUs. Additionally, spacing Link Frames relatively evenly keeps Link Slaves timing from drifting far from the Link Master, relative to spacing by wide gaps.

FIG. 11 depicts an exemplary TDMA page structure, where each TDMA frame is 16 timeslots long and the TDMA page is 23 frames long.

Figure 12:
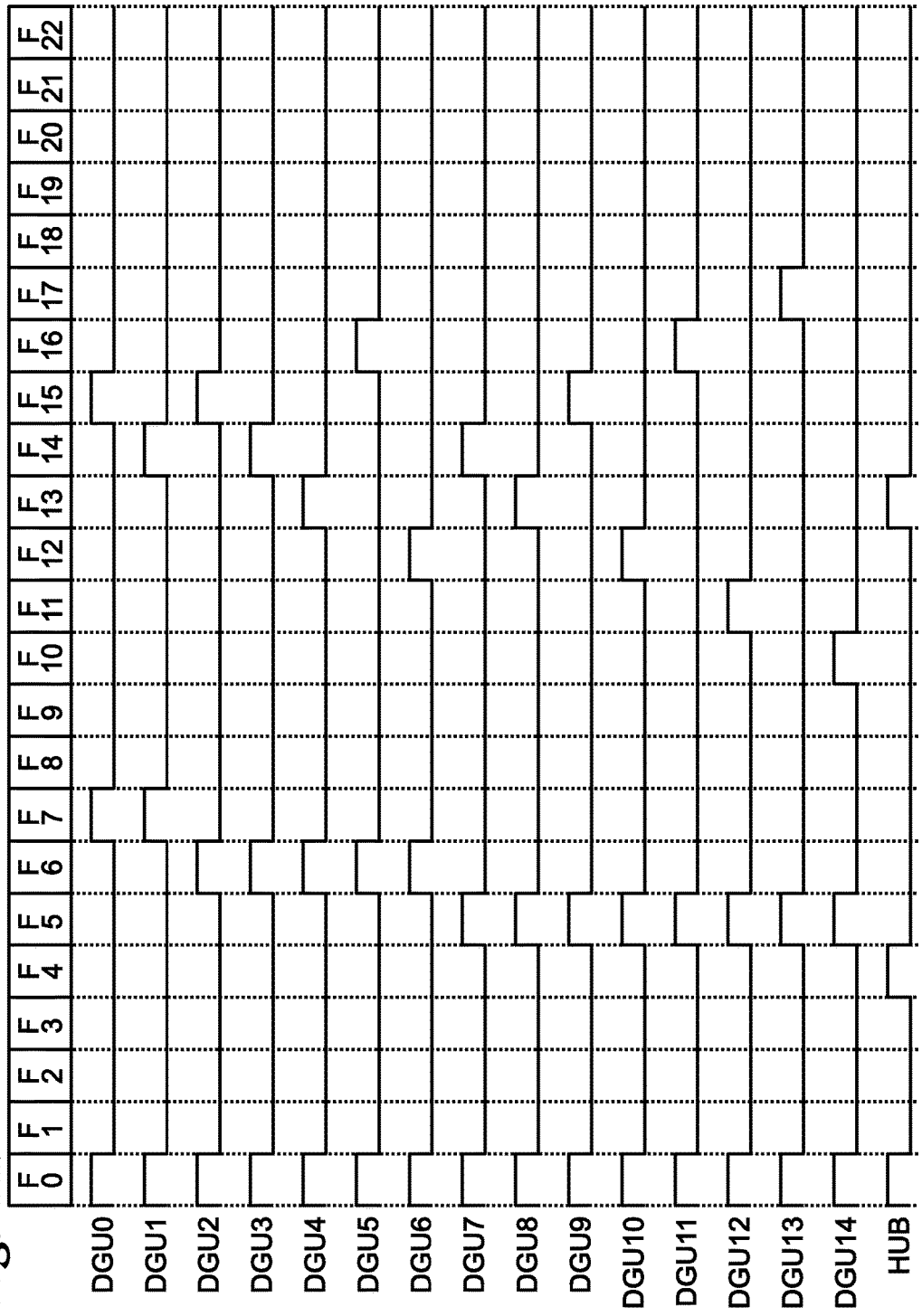
FIG. 12 shows the Link Frames in a TDMA page for each CCD in the system.

Table 1 lists the example's Link Frames in the TDMA page. FIG. 12 shows the Link Frames in a TDMA page for each CCD in the system. Other Link Frame spacing and page lengths are also possible. The only requirement is that the Link Frame spacing be incommensurate when considering TDMA page wrap around.

TABLE 1

| CCD | Frame Spacing | Link Frames |
|---|---|---|
| DGU0 | 7, 8, (8) | F0, F7, F15, (F0) |
| DGU1 | 7, 7, (9) | F0, F7, F14, (F0) |
| DGU2 | 6, 9, (8) | F0, F6, F15, (F0) |
| DGU3 | 6, 8, (9) | F0, F6, F14, (F0) |
| DGU4 | 6, 7, (10) | F0, F6, F13, (F0) |
| DGU5 | 6, 10, (7) | F0, F6, F16, (F0) |
| DGU6 | 6, 6, (11) | F0, F6, F12, (F0) |
| DGU7 | 5, 9, (9) | F0, F5, F14, (F0) |
| DGU8 | 5, 8, (10) | F0, F5, F13, (F0) |
| DGU9 | 5, 10, (8) | F0, F5, F15, (F0) |
| DGU10 | 5, 7, (11) | F0, F5, F12, (F0) |
| DGU11 | 5, 11, (7) | F0, F5, F16, (F0) |
| DGU12 | 5, 6, (12) | F0, F5, F11, (F0) |
| DGU13 | 5, 12, (6) | F0, F5, F17, (F0) |
| DGU14 | 5, 5, (13) | F0, F5, F10, (F0) |
| Hub | 4, 9, (10) | F0, F4, F13, (F0) |

Link Master Messages contain a Frame ID field identifying the index of the current Link Frame. The index spans the number of Link Frames in a TDMA page, plus one. The additional index is used when a CCD transmits a Link Master Message in a TDMA frame which is not one of its own Link Frames. The Frame ID enables receiving CCDs to determine the transmitting CCD's current TDMA frame in the current TDMA page, and thus establish TDMA frame synchronization with the link. For the example shown in Table 1, each CCD has 3 Link Frames, so the Frame ID needs to span 4 values, i.e. from 0 to 3.

The Link Master Message contains a Storage Active field to inform Storage Group DGUs that they should be storing their generated data into local memory. When a Link Master determines that storage should be active, it maintains that storage status for a predetermined time duration, such as four TDMA pages. This allows the storage status to remain relatively stable even if link messages from an Active Storage Group member are momentarily not received. When a Link Slave receives a true Storage Active Field, it maintains that storage status for a predetermined time duration, such as four TDMA pages. This allows the storage status to remain relatively stable even if the link transitions between Link Masters, when a current Link Master stops transmitting and another CCD transitions to be the new Link Master.

Data can be stored in any size data block in each DGU. Each data block in each DGU includes an identifier which enables data blocks from multiple DGUs to be time aligned with each other when later read from storage memory. The identifier is contained in the Storage ID field of the Link Master Message, enabling all DGUs to share the same identifier for data generated at the same time. The identifier can be fully provided in each Link Master Message, or it can be separated into parts with each part included in at least one of the Link Master Messages in a TDMA page. Distributing the identifier across a full TDMA page reduces the amount of data in any one Link Master Message, thus conserving battery power.

One example of a storage identifier is a number that consists of three fields, as shown in FIG. 5. The first field is the initial Link Master serial number. Each DGU in a Storage Group has a serial number assigned to it that is different from the serial number of any other DGU in the Storage Group. The initial Link Master serial number is the serial number of the Link Master that initiated a storage session, and it does not change during the recording session, even if the Link Master transitions from the session's initial Link Master CCD to a different Link Master CCD during the session. The second field is the initial Link Master session index. This is a number which increments by one for each session started by a given CCD. This number also does not change during a session, even if Link Master transitions occur. The third field is a block index. This number starts at zero and increments by one for each block stored during a session. Aligning the data block storage size with the TDMA page size enables one data block to be stored per TDMA page, and the block index to increment once per TDMA page.

A number of parameters are used to determine if a CCD should transition from a first Link Master to a second Link Master. These include the synchronization of the first and second links, the size of a link's Active Storage Group, the relative level of power resources, the first and second Link Master timeslot indexes, and the Active Storage Group members.

When a first CCD receives a Link Master Message from a second CCD, synchronization of the second CCD to the first CCD is determined by calculating the difference in time between when the second CCD's Link Master Message arrived at the first CCD and the expected time of that message's arrival and comparing that difference to a predetermined value, such as 10% of the timeslot period. The expected arrival time is equal to the second CCD's timeslot index multiplied by the timeslot period.

If a CCD's Active Storage Group is larger than half of the Storage Group, or if a CCD's Active Storage Group is equal to half of the Storage Group and contains the DGU with the lowest used timeslot index in the Storage Group (for example), then that CCD's link is designated as a dominant link. Using these criteria, any Storage Group can only have one dominant link. A CCD in a dominant link is not allowed to transition to a link which is not dominant. Since only the Link Master receives link messages from all Storage Group members, only the Link Master can determine if the link is dominant. However, other active CCDs need to know if they are in a dominant link in order to determine if they should transition to another unsynchronized link when they receive a Link Master Message from that unsynchronized link. Therefore, the Link Master Message contains a Dominant Link field indicating if the current link is dominant.

When a Link Master determines that it has a dominant link using the above criteria, it maintains that dominant link status for a predetermined time duration, such as two TDMA pages. This allows the dominant status to remain relatively stable even if link messages from an Active Storage Group member are momentarily not received. The CCD's dominant link status is refreshed every time the CCD determines that it has a dominant link.

To further aid devices in determining if they should transition from a first link to a second link, the Link Master Message also contains fields indicating the size of the link's Active Storage Group and the link resource level.

The Active Storage Group size is the number of DGUs in the Storage Group which are actively communicating with the Link Master CCD, plus one for the Link Master CCD itself. Actively communicating means that the Link Master CCD has received a Link Master Message or Link Slave Message from a Storage Group DGU within a predetermined previous time period, for example, within two TDMA page time periods. The Active Storage Group Size field needs to be large enough to hold a count greater than one half of the total number of DGUs that could possibly connect to a CCD. Holding a larger number is not required, since if a first CCD is connected to more than half the number of possible Storage Group DGUs, then all other CCD must be connected to fewer Storage Group DGUs than this first CCD. Since all Link Master devices, except for the hub, are connected to at least one active Storage Group DGU (i.e. themselves), one can be subtracted from the Active Storage Group size before transmitting if the Active Storage Group size is larger than zero. For example, if 15 DGU timeslots are available, then the Active Storage Group Size field needs to be able to hold the numbers 0 to 7.

When a first CCD receives a Link Master Message from a second CCD that is not synchronized to the first CCD's link, and the second CCD's link is more predominant than the first CCD's link, then the first CCD transitions to a Link Slave of the second CCD. The second CCD's link is more predominant than the first if the following three statements are true (Rule 7):

1. The second CCD is the Link Master of the second CCD's link;
2. Any of the following are true:
   a. The second CCD's Active Storage Group size is larger than first CCD's Active Storage Group size;
   b. The second CCD's Active Storage Group size is equal to the first CCD's Active Storage Group size AND the second CCD's link resource is greater than the first CCD's link resource;
   c. The second CCD's Active Storage Group size is equal to the first CCD's Active Storage Group size AND the second CCD's link resource is equal to the first CCD's link resource AND the second CCD's Link Master timeslot index is less than the first CCD's Link Master timeslot index.

The Link Master timeslot index is used above in Rule 7's Step 2c as a unique number to create a tie breaker between the two groups. Any other method of creating a unique number would also be valid.

While a CCD is not connected with a dominant link, the CCD must keep its receiver enabled when the CCD is not transmitting, so that the CCD can search for a Link Master which does have a dominant link. Since a CCD in a dominant link cannot transition to another link, devices in dominant links do not need to be able to receive messages from devices not in their link. Therefore, Link Masters in dominant links only need to enable their receiver during timeslots occupied by Storage Group members or the hub, and when receiving acknowledgements for data sent to the hub. Link Masters in dominant links disable their receiver during other timeslots, reducing power consumption. Link Slaves in dominant links only need to enable their receiver during their Link Master's timeslot and when receiving acknowledgements for data sent to the hub. Link Slaves in dominant links disable their receiver during other timeslots, reducing power consumption. The hub keeps its receiver enabled whenever it is not transmitting, so that it can receive Data Messages from any DGU, even if a DGU is not in the Storage Group.

Figure 13:
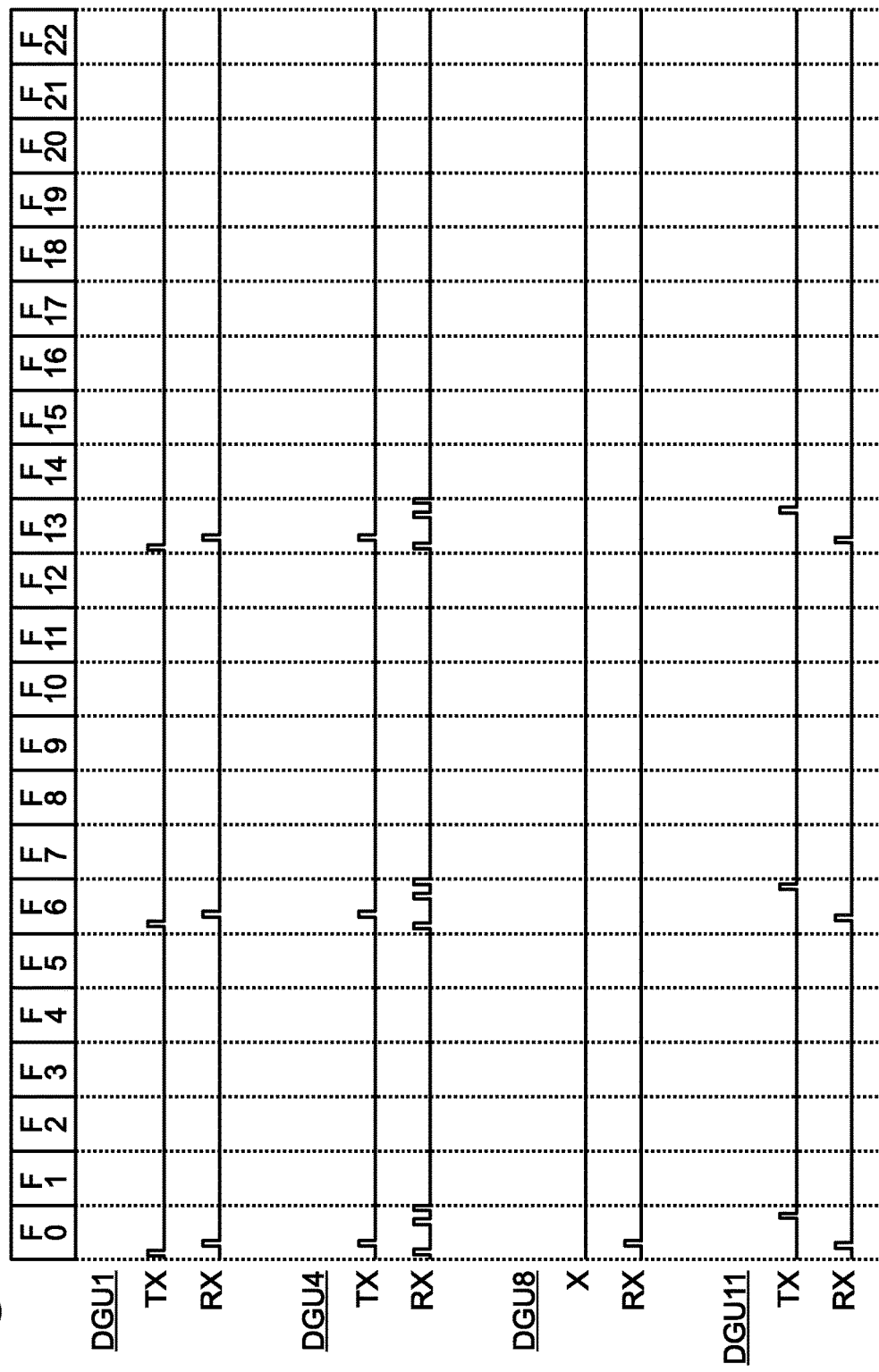
FIG. 13 is a diagram showing the transceiver TX (transmit) and RX (receiver) time periods in the exemplary system of FIG. 3 for a dominant link when the hub is not present.

FIG. 13 is a diagram showing the transceiver TX (transmit) and RX (receiver) time periods in the exemplary system of FIG. 3 for a dominant link when the hub is not present. Since DGU 300b is the Link Master, it enables its transmitter and transmits Link Master Messages during its timeslot in its Link Frames of F0, F6, and F13 (from Table 1). It also enables its receiver during the timeslots of the other Storage Group devices and the hub during its own Link Frames. Storage Group devices (DGUs 300a and 300d) enable their own transmitter and transmit Link Slave Messages during their own timeslots of the Link Master's Link Frames, and enable their receivers during the Link Master's timeslots of the Link Master's Link Frames. Devices which are not in the Storage Group (DGU 300c) do not enable their transmitters at all, and only occasionally enable their receiver to detect if the hub is present.

Figure 14:
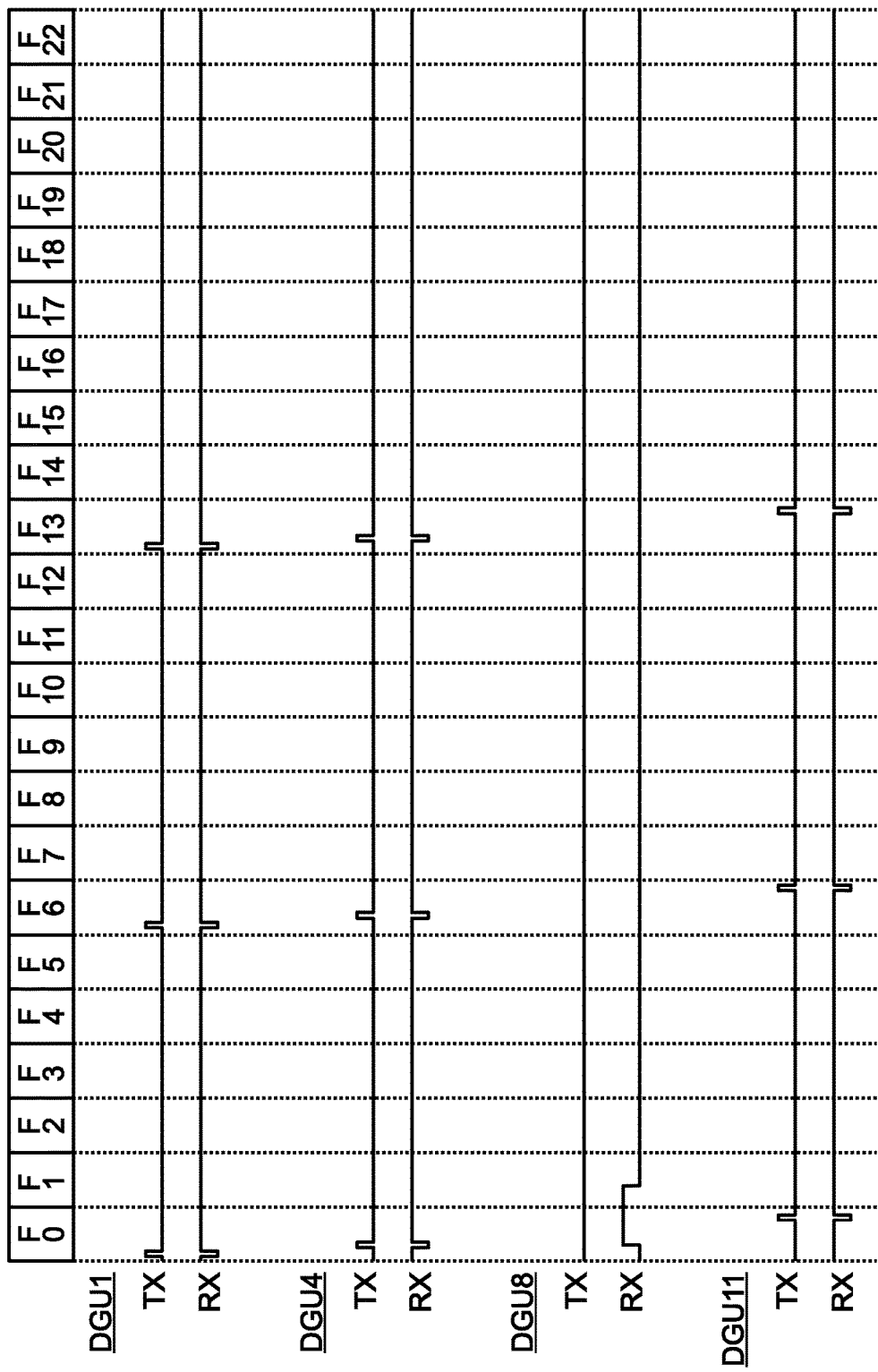
FIG. 14 is a diagram depicting transceiver TX and RX time periods in the system of FIG. 3 for a non-dominant link.

FIG. 14 is a diagram depicting transceiver TX and RX time periods in the system of FIG. 3 for a non-dominant link. In contrast to the dominant link case, FIG. 14 shows how devices in a non-dominant link enable their receiver whenever they are not transmitting, in order to locate a more predominant link. Devices which are not in the Storage Group (DGU 300c) still only occasionally enable their receiver to detect if the hub is present.

When a Link Slave is not an MCD and does not receive Link Master Messages for a predetermined time duration, such as two TDMA pages, then the Link Slave transitions to the Link Ungrouped state (Rule 8).

When a Link Slave is an MCD and it does not receive Link Master Messages for a predetermined time duration, such as two TDMA pages, then the Link Slave transitions to a Link Master (Rule 9).

Link Masters include their link resource level in the Link Master Message, enabling Link Slaves to compare their own link resource level to the Link Master's link resource level. When a Link Slave is an MCD and it determines that its link resource level is sufficiently larger, for example 10% larger, than the current Link Master's link resource level, then the Link Slave transitions to a Link Master becoming the new Link Master (Rule 10).

Initially, the new Link Master will have no Link Slaves, because when it was a Link Slave, it did not receive link messages from any devices other than its own Link Master. The new Link Master fills the Dominant Link and Storage Active fields of its transmitted Link Master Messages with the values that the previous Link Master transmitted for a predetermined time duration, such as two TDMA pages, while other devices transition to this new Link Master.

When a Link Slave receives a Link Master Message synchronous with its current link timing and the message's link resource level is larger than the Link Slave's current Link Master's link resource level, then the Link Slave transitions its current Link Master to the new Link Master (Rule 11).

When a first Link Master receives a Link Master Message from a second Link Master synchronous with its current link timing and the message's link resource level is larger than the first Link Master's link resource level, or the message's link resource level is equal to the first Link Master's link resource level and the message's Link Master TDMA timeslot index is smaller than the first Link Master's TDMA timeslot index, then the first Link Master transitions to a Retiring Link Master and also transitions its current Link Master to the new Link Master (Rule 12).

Retiring Link Masters transmit Link Master Messages in both their own Link Frames and in the Link Frames of their new Link Master. They fill the Master Timeslot field of their Link Master Messages with the timeslot index of their new Link Master to assist their Link Slaves in transitioning to the new Link Master. If a CCD is a Retiring Link Master, and for a predetermined time duration, such as two TDMA pages, the CCD receives no Link Slave messages from an MCD with the message's Master Timeslot value set to the CCD's timeslot index, and further, the CCD has received a Link Master Message less than a predetermined time duration earlier, such as two TDMA pages, then the CCD transitions to a Link Slave (Rule 13).

If a CCD is a Retiring Link Master, and for a predetermined time duration, such as two TDMA pages, the CCD receives no Link Slave messages from an MCD with the message's Master Timeslot value set to the CCD's timeslot index, and the CCD has not received a Link Master Message less than a predetermined time duration earlier, such as two TDMA pages, then the CCD transitions to the Link Ungrouped state (Rule 14).

Figure 15:
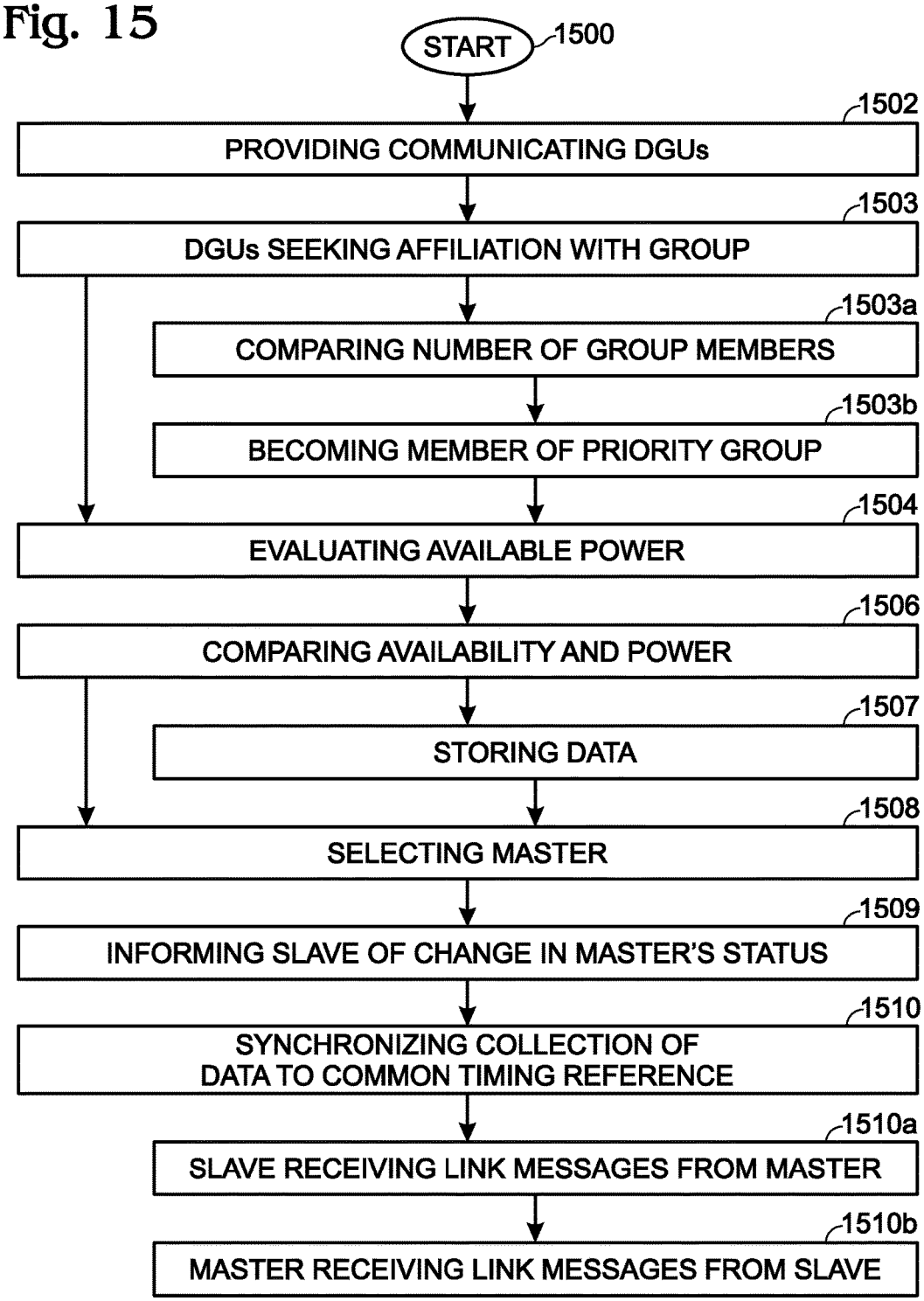
FIG. 15 is a flowchart illustrating method for distributed data collection synchronization.

FIG. 15 is a flowchart illustrating a method for distributed data collection synchronization. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. Generally however, the method follows the numeric order of the depicted steps. The method starts at Step 1500.

Step 1502 provides a plurality of communicating DGUs capable of data storage, each having a consumable power resource. In Step 1504 each DGU evaluates its available power. In Step 1506 the DGUs compare their availability and power resources. In response to the DGUs comparing their availability and power resources, a master DGU and a slave DGU are determined in Step 1508. In Step 1510 slave DGUs synchronize their collection of data to a common timing reference supplied by their master DGU. In one aspect, the DGUs comparing their availability in Step 1504 includes a first DGU selecting itself as a master DGU in response to receiving no link status message from a master DGU for a first predetermined duration of time after reset, or receiving no link status message from a master DGU for a second predetermined duration of time when the first DGU is a slave. In another aspect, DGUs synchronizing their collection of data to a common timing reference supplied by the master DGU (Step 1510) includes the slave DGUs and retiring master DGUs updating their communication, data sampling, and data storage timing based upon the contents and timing of a received Link Master Message. In yet another aspect, DGUs synchronizing their collection of data to a common timing reference supplied by the master DGU (Step 1510) includes the slave DGUs, master DGUs, and retiring master DGUs all periodically synchronously storing a shared identifier uniquely indicating the time alignment of distributed stored data when data storage is active.

In one aspect, the DGUs comparing their power resources in Step 1504 includes a slave first DGU comparing its own available power resources to the available power resources of its master second DGU. Then, Step 1508 selects the first DGU as the master DGU when the available power resources of the first DGU are greater than the available resources of the second DGU by a predetermined amount, and in Step 1510 the slave second DGU synchronizes to a timing reference supplied by the master first DGU.

Similarly, in Step 1504 a synchronized DGU may compare the available power resources of a master first DGU and a master second DGU. As noted above, a synchronized DGU is a member of a group (actively communicating DGUs)

acting in the capacity of either a master DGU or a slave DGU. Step 1508 selects the first DGU as the master of the synchronized DGU when the available power resources of the first DGU are greater than the available power resources of the second DGU.

If, in Step 1508 a master first DGU selects a master second DGU as its master, in Step 1509 the first DGU informs a slave third DGU, previously synchronized to the first DGU timing reference, that the second DGU is now the master of the first DGU.

In one aspect prior to every comparison of availability and power resources in Step 1504, in Step 1503 the DGUs seek affiliation with a group of DGUs. Step 1503 may include the following substeps. In Step 1503a a first DGU in a first group of DGUs compares the number of members in the first group to the number of members in a second group. In Step 1503b the first DGU becomes a slave to a master in the second group in response to one of the following conditions establishing the priority of the second group:

the second group having more members; or, the second group having the same number of members as the first group, and the available power resources of the master DGU of the second group are greater than those of the master DGU of the first group; or, the second group having the same number of members as the first group, the available power resources of the master DGU of the second group being equal to those of the master DGU of the first group, and the master DGU of the second group having a unique identifier (UI) with greater significance than the UI of the master DGU of the first group.

Providing the plurality of communicating DGUs in Step 1502 includes providing DGUs with assigned transmission slots in a TDMA communications system. Then, the slave DGUs synchronizing their collection of data to the common timing reference supplied by the master DGU in Step 1510 may include the following sub-steps. In Step 1510a each slave DGU periodically receives a link status message from a master DGU, whose contents and arrival time inform the slave DGU of current link timing from the perspective of the transmitting master DGU. In Step 1510b the master DGU periodically receives link status messages from their slave DGUs informing the master DGU of their link connectivity.

Additionally, Step 1502 provides a TDMA communications system with a TDMA page including a first plurality of frames, where each frame includes a plurality of time slots. Each DGU is assigned a master link status transmission frame in a unique frame pattern including a second plurality of frames, less than the first plurality. Thus, for each pair of DGUs, at least one non-overlapping master link status transmission frame per TDMA page is guaranteed, independent of any time alignment of TDMA page overlapping.

Step 1510a, where each slave DGU periodically receives a link status message from a master DGU, further includes, when a first DGU is a slave, transmitting link status messages only in the first DGU's assigned transmission slot during the assigned Link Frames of the first DGU's master. Step 1510b, where the master DGU periodically receiving link status messages from their slave DGUs, further includes, when the first DGU is a master, the first DGU transmitting link status messages only during its assigned transmission slot of its assigned Link Frames. Alternatively, when the first DGU is a retiring master, the first DGU transmits link status messages only during its assigned transmission slot of both the assigned Link Frames of the first DGU's master and the assigned Link Frames of the first DGU itself.

In another aspect, the DGUs periodically receiving a link status messages (Steps 1510a and 1510b) includes the DGUs selectively disabling their receivers in response to being a member of a dominant group of communicating DGUs. A dominant group includes either more than half the number of DGUs capable of data storage, or half the number of DGUs capable of data storage and the DGU with the most significant unique identifier (UI). Further, in Steps 1510a and 1510b a DGU enables its receiver whenever it is not transmitting, if it is a member of a non-dominant group. In greater detail, if the first DGU is a member of a dominant group, it only enables its receiver to receive link status messages when: as a slave, during the transmission slot of the first DGU's master DGU in the master DGU's Link Frames; as a master, during the transmission slots of the first DGU's slave DGUs and the hub in the first DGU's Link Frames; or as a retiring master, during both the transmission slot of the first DGU's master DGU in its master DGU's Link Frames, and the transmission slots of the first DGUs slave DGUs in the first DGU's Link Frames.

In a different aspect, in Step 1507 the plurality of communicating DGUs only store data when the plurality includes:

a group comprising a minimum number of synchronized DGUs, where a synchronized DGU is either a master DGU or slave DGU; or, a group comprising a required subset of synchronized DGUs; or, a group comprising both a minimum number of synchronized DGUs and a required subset of synchronized DGUs.

A system and method have been provided for the synchronization of distributed data collection. Examples of particular message structures, processors, and hardware units have been presented to illustrate the invention. However, the invention is not limited to merely these examples. Other variations and embodiments of the invention will occur to those skilled in the art.

I claim:

1. A method for distributed data collection synchronization, the method comprising:

providing a plurality of communicating data generation units (DGUs) capable of data storage, each having a consumable power resource;

each DGU evaluating its available power;

the DGUs comparing their availability and power resources;

in response to the DGUs comparing their availability and power resources, determining a master DGU and at least one slave DGU; and the slave DGUs synchronizing their collection of data to a common timing reference supplied by their master DGU.

2. The method of claim 1, wherein the DGUs comparing their availability includes a first DGU selecting itself as a master DGU in response to receiving no link status message from a master DGU for a first predetermined duration of time after reset, or receiving no link status message from a master DGU for a second predetermined duration of time when the first DGU is a slave DGU.

3. The method of claim 1, wherein the DGUs comparing their power resources includes a slave first DGU comparing its own available power resources to the available power resources of its master second DGU;

wherein determining the master DGU includes selecting the first DGU as the master DGU when the available power resources of the first DGU are greater than the available power resources of the second DGU by a predetermined amount; and wherein the slave DGUs synchronizing their collection of data to a common timing reference supplied by their master DGU includes the slave second DGU synchronizing to a timing reference supplied by the master first DGU.

4. The method of claim 1, wherein the DGUs comparing their power resources includes a synchronized DGU comparing the available power resources of a master first DGU and a master second DGU, where a synchronized DGU is a member of a group acting in the capacity of either a master DGU or a slave DGU; and wherein determining the master DGU includes the synchronized DGU selecting the first DGU as the master of the synchronized DGU when the available power resources of the first DGU are greater than the available power resources of the second DGU.

5. The method of claim 4 further comprising:

in response to a master first DGU selecting a master second DGU as its master, the first DGU informing a slave third DGU, previously synchronized to the first DGU timing reference, that the second DGU is now the master of the first DGU.

6. The method of claim 1 further comprising:

prior to every comparison of availability and power resources, the DGUs seeking affiliation with a group of DGUs.

7. The method of claim 6, wherein seeking affiliation with a group of DGUs includes:

a first DGU in a first group comparing the number of members in the first group to the number of members in a second group; and the first DGU becoming a slave to a master in the second group in response to:
 the second group having more members; or
 the second group having the same number of members as the first group, and the available power resources of the master DGU of the second group are greater than those of the master DGU of the first group; or
 the second group having the same number of members as the first group, the available power resources of the master DGU of the second group being equal to those of the master DGU of the first group, and the master DGU of the second group having a unique identifier (UI) with greater significance than the UI of the master DGU of the first group.

8. The method of claim 1, wherein providing the plurality of communicating DGUs includes providing DGUs with assigned transmission slots in a time division multiple access (TDMA) communications system;

wherein the slave DGUs synchronizing their collection of data to the common timing reference supplied by the master DGU includes:
 each slave DGU periodically receiving a link status message from a master DGU, whose contents and arrival time inform the slave DGU of current link timing from the perspective of the transmitting master DGU; and
 the master DGU periodically receiving link status messages from their slave DGUs informing the master DGU of their link connectivity.

9. The method of claim 8, wherein providing the DGUs with assigned transmission slots in a TDMA communications system includes:

providing a TDMA page including a first plurality of frames, where each frame includes a plurality of time slots;

assigning each DGU a second plurality of master Link Frames in a unique frame pattern, less than the first plurality; and for each pair of DGUs, guaranteeing at least one non-overlapping master link status transmission frame per TDMA page, independent of any time alignment of TDMA page overlapping.

10. The method of claim 9, wherein each slave DGU periodically receiving a link status message from a master DGU includes, when a first DGU is a slave, transmitting link status messages only in the first DGU's assigned transmission slot during the assigned Link Frames of the first DGU's master;

wherein the master DGU periodically receiving link status messages from their slave DGUs includes:
 when the first DGU is a master, the first DGU transmitting link status messages only during its assigned transmission slot of its assigned Link Frames; and
 when the first DGU is a retiring master, the first DGU transmitting link status messages only during its assigned transmission slot of both the assigned Link Frames of the first DGU's master and the assigned Link Frames of the first DGU itself.

11. The method of claim 10, wherein the DGUs periodically receiving a link status messages includes the DGUs selectively disabling their receivers in response to being a member of a dominant group of communicating DGUs, where a dominant group includes:
 more than half the number of DGUs capable of data storage; or
 half the number of DGUs capable of data storage and the DGU with the most significant unique identifier (UI).

12. The method of claim 11, wherein each DGU periodically receiving the link status messages includes a DGU enabling its receiver whenever it is not transmitting, if it is a member of a non-dominant group.

13. The method of claim 11, wherein the DGUs periodically receiving the link status messages includes, in response to the first DGU being a member of a dominant group, only enabling the first DGU's receiver to receive link status messages when:
 the first DGU is a slave, during the transmission slot of the first DGU's master DGU in the master DGU's Link Frames;
 the first DGU is a master, during the transmission slots of the first DGU's slave DGUs in the first DGU's Link Frames; and
 the first DGU is a retiring master, during both the transmission slot of the first DGU's master DGU in its master DGU's Link Frames, and the transmission slots of the first DGUs slave DGUs in the first DGU's Link Frames.

14. The method of claim 1 further comprising:

the plurality of communicating DGUs only storing data when the plurality includes:
 a group comprising a minimum number of synchronized DGUs, where a synchronized DGU is either a master DGU or a slave DGU; or
 a group comprising a required subset of synchronized DGUs; or
 a group comprising both a minimum number of synchronized DGUs and a required subset of synchronized DGUs.

15. The method of claim 1, wherein the slave DGUs synchronizing their collection of data to a common timing reference supplied by the master DGU includes the slave DGUs, master DGUs, and retiring master DGUs all periodically synchronously storing a shared identifier uniquely indicating the time alignment of distributed stored data.

16. A system for distributed data collection synchronization, the system comprising:
a plurality of communicating data generation units (DGUs) capable of data storage, including a master DGU and a slave DGU, each DGU comprising:
a processor;
a non-transitory memory;
a transmitter and receiver;
a resource;
a synchronization application, enabled as a sequence of processor executable steps and stored in the memory, evaluating the availability of DGUs and their consumable power, and selecting the master DGU and slave DGU in response to the evaluation; and
wherein the slave DGU synchronizes its collection of data, for storage in the memory, to a common timing reference supplied by its master DGU.

17. The system of claim 16, wherein a first DGU selects itself as a master DGU in response to receiving no link status message from a master DGU for a first predetermined duration of time after reset, or receiving no link status message from a master DGU for a second predetermined duration of time when the first DGU is a slave DGU.

18. The system of claim 16, wherein a slave first DGU compares its own available power resources to the available power resources of its master second DGU, and selects itself as the master DGU when the available power resources of the first DGU are greater than the available power resources of the second DGU by a predetermined amount; and
wherein the second DGU, acting as a slave DGU synchronizes to a timing reference supplied by the master first DGU.

19. The system of claim 16, wherein a synchronized DGU compares the available power resources of a master first DGU and a master second DGU, where a synchronized DGU is a member of a group acting in the capacity of either a master DGU or a slave DGU, and selects the first DGU as its master when the available power resources of the first DGU are greater than the available power resources of the second DGU.

20. The system of claim 19, wherein a master first DGU selects a master second DGU as its master, and informs a slave third DGU, previously synchronized to the first DGU timing reference, that the second DGU is now the master of the first DGU.

21. The system of claim 16, wherein each DGU seeks affiliation with a group of DGUs prior to every evaluation of DGU availability and consumable power.

22. The system of claim 21, wherein a first DGU in a first group compares the number of members in the first group to the number of members in a second group, and becomes a slave to a master in the second group in response to:
the second group having more members; or
the second group having the same number of members as the first group, and the available power resources of the master DGU of the second group are greater than those of the master DGU of the first group; or
the second group having the same number of members as the first group, the available power resources of the master DGU of the second group being equal to those of the master DGU of the first group, and the master DGU of the second group having a unique identifier (UI) with greater significance than the UI of the master DGU of the first group.

23. The system of claim 16, wherein each DGU is assigned transmission slots in a time division multiple access (TDMA) communications system;
wherein each slave DGU periodically receives a link status message from a master DGU, whose contents and arrival time inform the slave DGU of current link timing from the perspective of the transmitting master DGU; and
wherein the master DGU periodically receives link status messages from their slave DGUs informing the master DGU of their link connectivity.

24. The system of claim 23, wherein each DGU is assigned:
a TDMA page including a first plurality of frames, where each frame includes a plurality of time slots; and
a second plurality of master Link Frames in a unique frame pattern, less than the first plurality, guaranteeing for each pair of DGUs at least one non-overlapping master link status transmission frame per TDMA page, independent of any time alignment of TDMA page overlapping.

25. The system of claim 24, wherein a first DGU, acting as a slave DGU, transmits link status messages only in the first DGU's assigned transmission slot during the assigned Link Frames of the first DGU's master;
wherein the first DGU, acting as a master DGU, transmits link status messages only during its assigned transmission slot of its assigned Link Frames; and
wherein the first DGU, acting as a retiring master DGU, transmits the link status messages only during its assigned transmission slot of both the assigned Link Frames of the first DGU's master and the assigned Link Frames of the first DGU itself.

26. The system of claim 25, wherein the DGUs selectively disable their receivers in response to being a member of a dominant group of communicating DGUs, where a dominant group includes:
more than half the number of DGUs capable of data storage; or
half the number of DGUs capable of data storage and the DGU with the most significant unique identifier (UI).

27. The system of claim 26, wherein each DGU enables its receiver whenever it is not transmitting, when it is a member of a non-dominant group.

28. The system of claim 26, wherein the first DGU, as a member of a dominant group, only enables its receiver to receive link status messages when:
the first DGU is a slave, during the transmission slot of the first DGU's master DGU in the master DGU's Link Frames;
the first DGU is a master, during the transmission slots of the first DGU's slave DGUs in the first DGU's Link Frames; or
the first DGU is a retiring master, during both the transmission slot of the first DGU's master DGU in its master DGU's Link Frames, and the transmission slots of the first DGUs slave DGUs in the first DGU's Link Frames.

29. The system of claim 16, wherein the DGUs only store data when a group of DGUs comprises;
a minimum number of synchronized DGUs, where a synchronized DGU is either a master DGU or slave DGU; or
a required subset of synchronized DGUs; or both a minimum number of synchronized DGUs and a required subset of synchronized DGUs.

30. The system of claim 16, wherein slave DGUs, master DGUs, and retiring master DGUs all periodically synchronously store a shared identifier uniquely indicating the time alignment of distributed stored data.

* * * * *

UNITED STATES PATENT AND TRADEMARK OFFICE
CERTIFICATE OF CORRECTION

PATENT NO. : 10,375,660 B2
APPLICATION NO. : 15/355152
DATED : August 6, 2019
INVENTOR(S) : Bryan Hallberg Page 1 of 1

It is certified that error appears in the above-identified patent and that said Letters Patent is hereby corrected as shown below:

On the Title Page

On page 2, under the heading of Related U.S. Application Data should read:
(63) Continuation-in-part of application No. 15/155,943, filed on May 16, 2016, which is a continuation-in-part of application No. 15/091,869, filed on Apr. 6, 2016 now abandoned, which is a continuation-in-part of application No. 14/873,946, filed on Oct. 2, 2015, now Pat. No. 9,846,040, which is a continuation-in-part of application No. 14/742,852, filed on Jun. 18, 2015, which is a continuation-in-part of application No. 14/707,194, filed on May 8, 2015, now Pat. No. 9,450,681.

Signed and Sealed this
Seventh Day of April, 2020

Andrei Iancu
*Director of the United States Patent and Trademark Office*